(12) United States Patent
Revishvili et al.

(10) Patent No.: US 8,660,639 B2
(45) Date of Patent: *Feb. 25, 2014

(54) METHOD OF NONINVASIVE ELECTROPHYSIOLOGICAL STUDY OF THE HEART

(75) Inventors: Amiran Shotaevich Revishvili, Moscow (RU); Vitaliy Viktorovich Kalinin, Voronezh (RU); Alexander Viktorovich Kalinin, Voronezh (RU)

(73) Assignee: "AMYCARD" LLC, Moscow (RU)

( * ) Notice: Subject to any disclaimer, the term of this patent is extended or adjusted under 35 U.S.C. 154(b) by 25 days.

This patent is subject to a terminal disclaimer.

(21) Appl. No.: 12/623,618

(22) Filed: Nov. 23, 2009

(65) Prior Publication Data

US 2011/0275921 A1    Nov. 10, 2011

(30) Foreign Application Priority Data

Nov. 27, 2008    (RU) ................. 2008146992

(51) Int. Cl.
*A61B 5/0402* (2006.01)
(52) U.S. Cl.
USPC ........................................ 600/509
(58) Field of Classification Search
USPC ................. 600/508, 509, 512, 513
See application file for complete search history.

(56) References Cited

U.S. PATENT DOCUMENTS

| 7,016,719 B2 | 3/2006 | Rudy et al. | |
|---|---|---|---|
| 2012/0004561 A1* | 1/2012 | John | 600/508 |

OTHER PUBLICATIONS

Sulimov, et al., "Transesophageal Cardiac Electrostimulation," Meditsina, pp. 78-79 (2001).
Revishvili, et al., "Electrophysiological Diagnostics and Interventional Treatment of Complex Cardiac Arrhythmias with Use of the System of Three-Dimensional Electro-Anatomical Mapping," pp. 32-37 (2003).
Pokushalov, et al., "Radio-Frequency Transpericardial Catheter Ablation of Ventricular Tachycardia", Vestnik arimologii, No. 44, pp. 58-62 (2006).
Titomir, et al., "Noninvasive Electrocardiotopography," pp. 97-111 (2003).
Nelson, et al., "The Theoretical Basis of Electrocardiology," Meditsina, pp. 346-350 (1979).
Shakin, "Computational Electrocardiography," Nauka, pp. 64-65 (1981).
Kalinin, "Use of ECG Recorded through a Subclavian Catheter for Differential Diagnosing Tachyarrhythmias," Proceedings of the 4th Session of the Moscow Society of Anesthesiologists and Resuscitators, Mar. 26, 2004.
Golnik, et al., "Construction and Application of Preprocessor for Generation, Performance Control, and Optimization of Triangulation Grids of Contact Systems," pp. 1-25 (2004).
Denisov, "Introduction to Theory of Inverse Problems," Moscow University Publishing House, pp. 22-43 (1994).
Tikhonov, et al., "Methods of Solution of Incorrect Problems," Nauka, pp. 53-127 (1979).

(Continued)

*Primary Examiner* — George Evanisko
(74) *Attorney, Agent, or Firm* — Ladas & Parry LLP

(57) ABSTRACT

The invention relates to medicine, namely to cardiology, cardiovascular surgery, functional diagnosis and clinical electrophysiology of the heart. The invention consists in reconstructing electrograms, whose experimental registration requires an invasive access, by computational way on unipolar ECGs recorded at 80 and more points of the chest surface. An application of the method allows one to improve the accuracy of non-invasive diagnosis of cardiac rhythm disturbances and other cardio-vascular diseases.

12 Claims, 25 Drawing Sheets

(56) References Cited

OTHER PUBLICATIONS

Titomir, et al., "Mathematical Modeling of the Cardiac Bioelectric Generator," Nauka, pp. 329-331 (1999).

Lacroute, "Fast Volume Rendering Using a Shear-Warp Factorization of the Viewing Transformation," Computer Systems Laboratory, Depts. of Electrical Engineering and Computer Science, Stanford University, pp. 29-43 (1995).

Lorensen, et al., "Marching Cubes: A High Resolution 3D Surface Construction Algorithm," Computer Graphics, vol. 21, No. 4, pp. 163-169 (1987).

Saad, "Iterative Methods for Sparse Linear Systems," Second Edition with Corrections, pp. 2-21, 157-172 (Jul. 2000).

Rudy, et al., "The Inverse Problem in Electrocardiography: Solutions in Terms of Epicardial Potentials," Crit Rev Biomed Eng., pp. 215-268 (1988); Abstract.

Berger, et al., "Single-Beat Noninvasive Imaging of Cardiac Electrophysiology of Ventricular Pre-Excitation," Journal of the American College of Cardiology, pp. 2045-2052 (2006).

Lo, "Volume Discretization into Tetrahedra—II. 3D Triangulation by Advancing Front Approach," Computers & Structures, vol. 39, Issue 5, pp. 501-511(1991); Abstract.

Rassineux, "3D Mesh Adaption. Optimization of Tetrahedral Meshes by Advancing Front Technique," Computer Methods in Applied Mechanics and Engineering 141, pp. 335-354 (1997).

Yoshida, "Applications of Fast Multipole Method to Boundary Integral Equation Method," Dept. of Global Environment Eng., Kyoto Univ., Japan, pp. 84-86 (Mar. 2001).

Kazhdan, et al., "Poisson Surface Reconstruction," Eurographics Symposium on Geometry Processing (2006).

Schilling, et al., "Endocardial Mapping of Atrial Fibrillation in the Human Right Atrium Using a Non-contact Catheter," European Heart Journal, pp. 550-564 (2000).

Ramanathan, et al., "Noninvasive Electrocardiographic Imaging for Cardiac Electrophysiology and Arrhythmia," Nature Medicine, pp. 1-7 (2004).

Brebbia, et al., "Boundary Element Techniques: Theory and Applications in Engineering," Springer-Verlag, Chapter 2, pp. 54-122 (1984), with English translation.

MacLeod, et al., "Recent Progress in Inverse Problems in Electrocardiology," Nora Eccles Harrison Cardiovascular Research and Training Institute, University of Utah, pp. 1-20, 1998.

\* cited by examiner

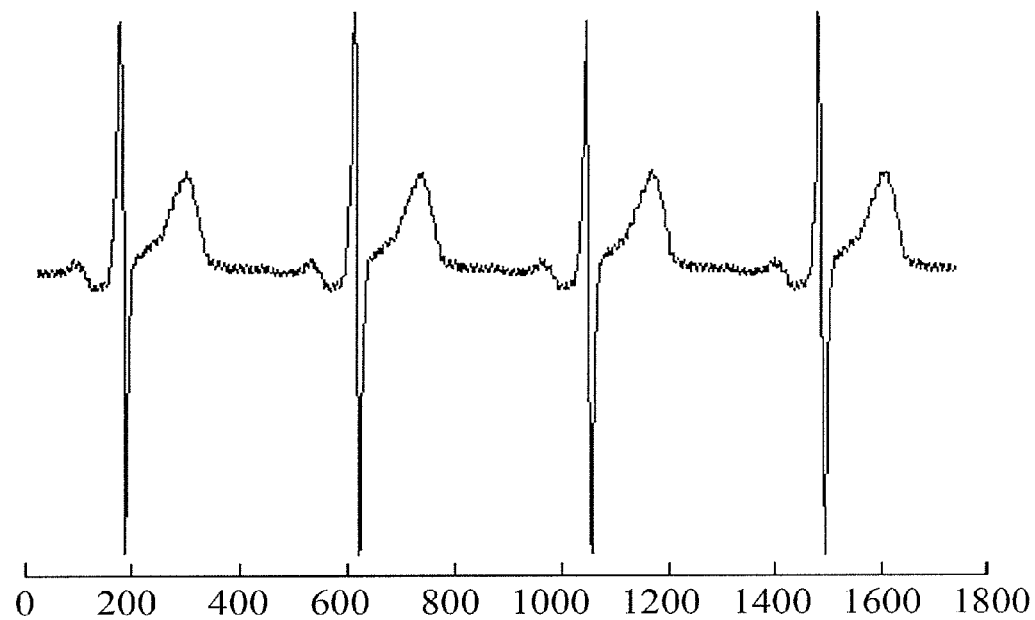
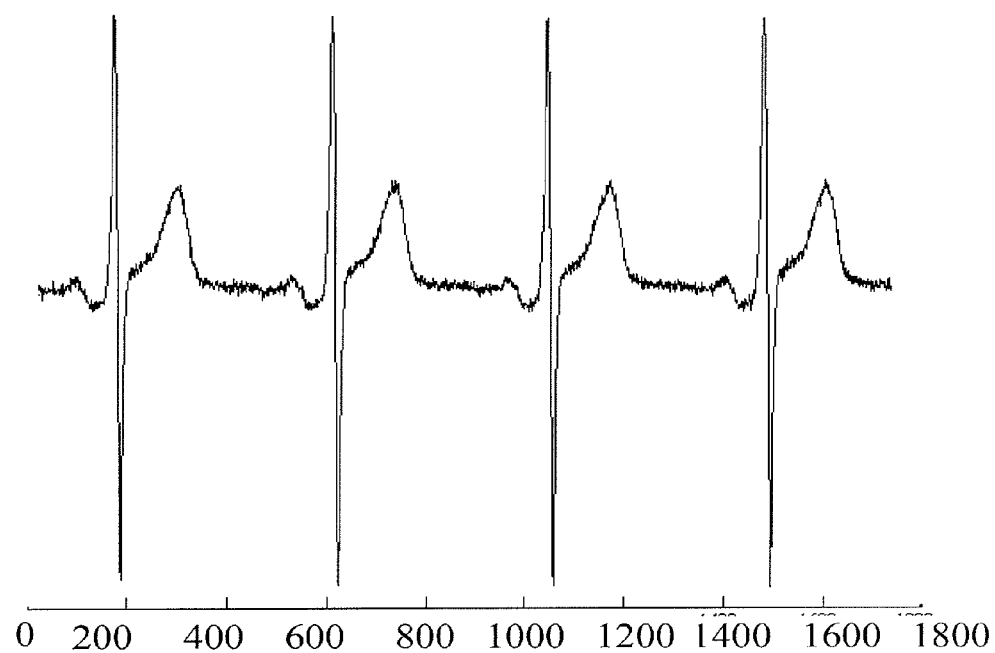
Fig. 5

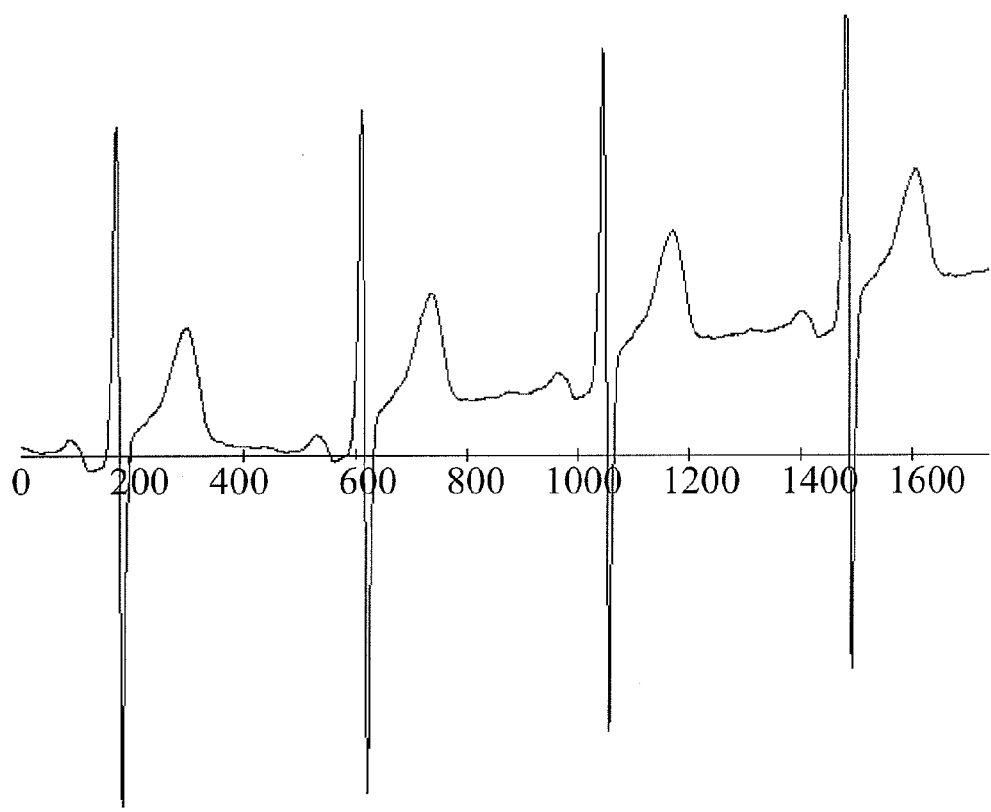
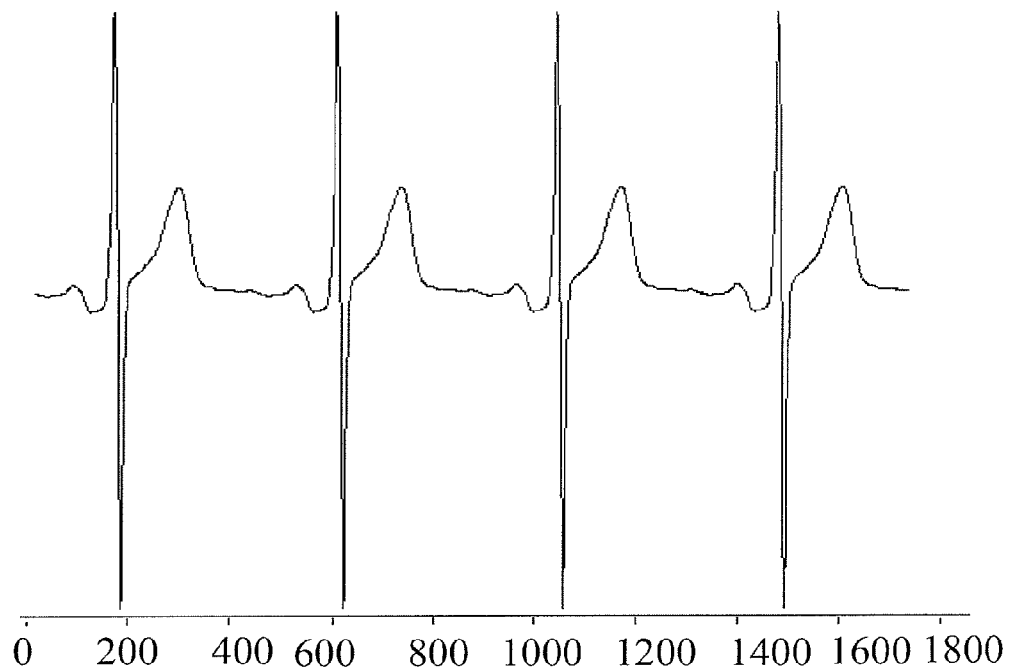
Fig. 5 (continued)

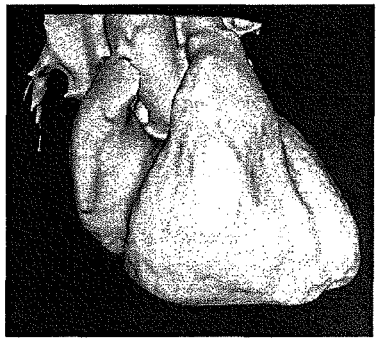
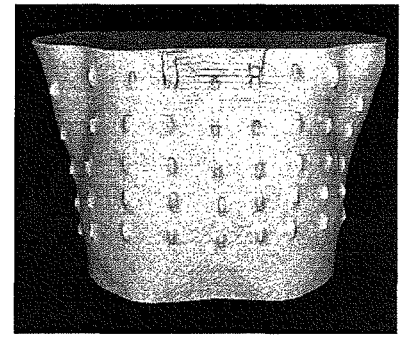
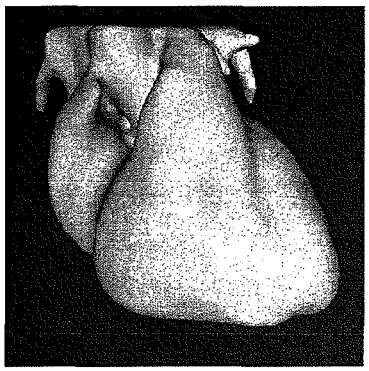
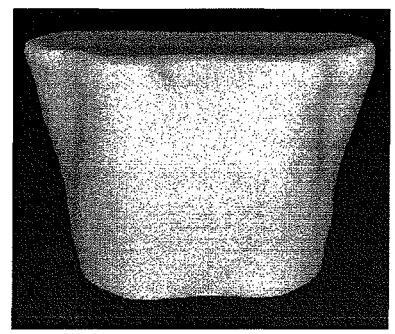
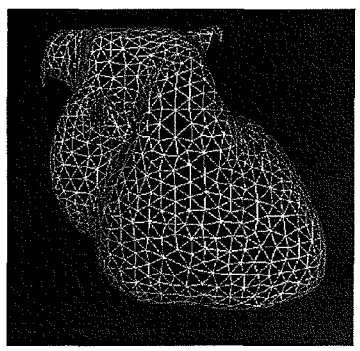
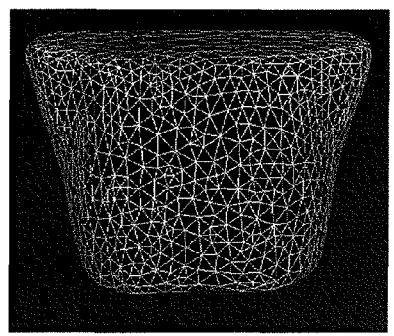
Fig. 8

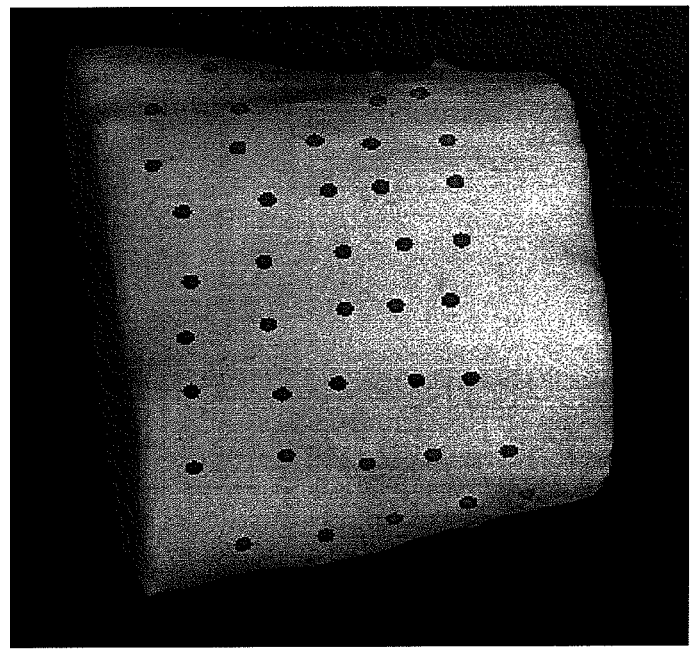
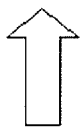
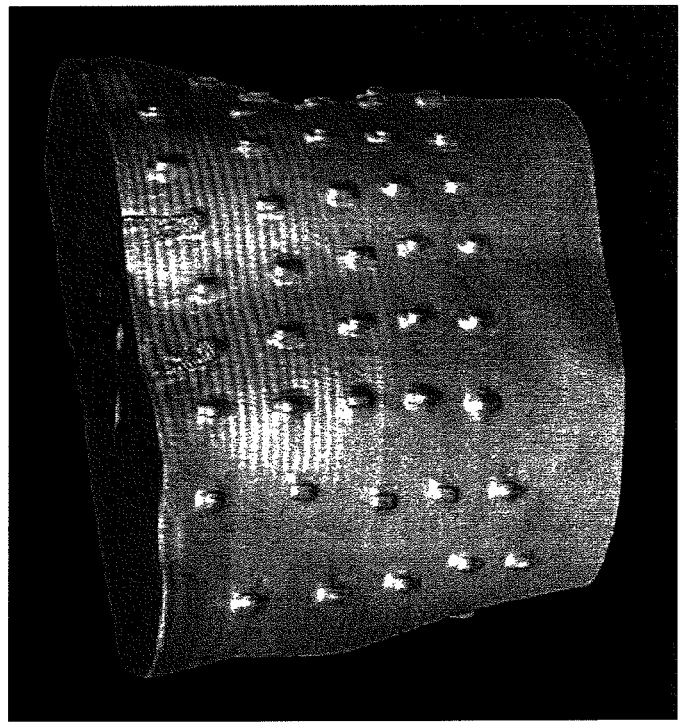
Fig. 9

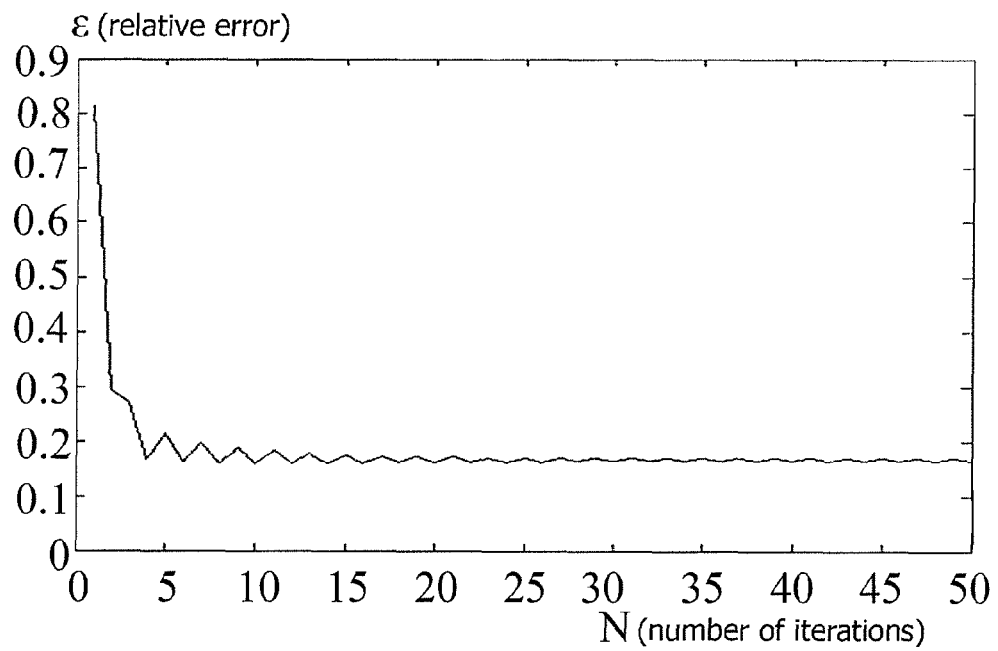
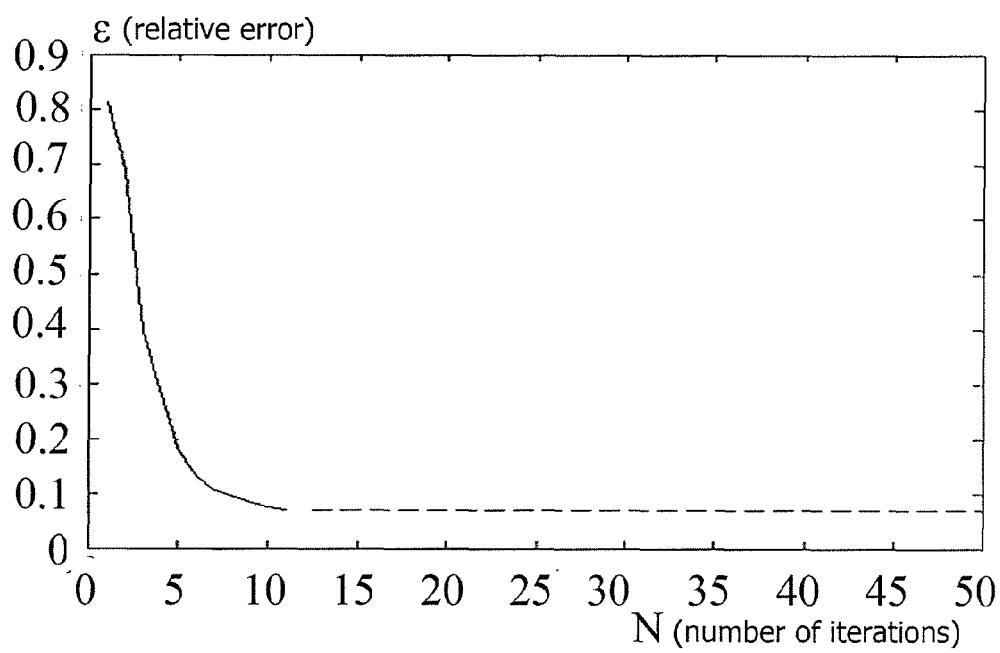
Fig. 12

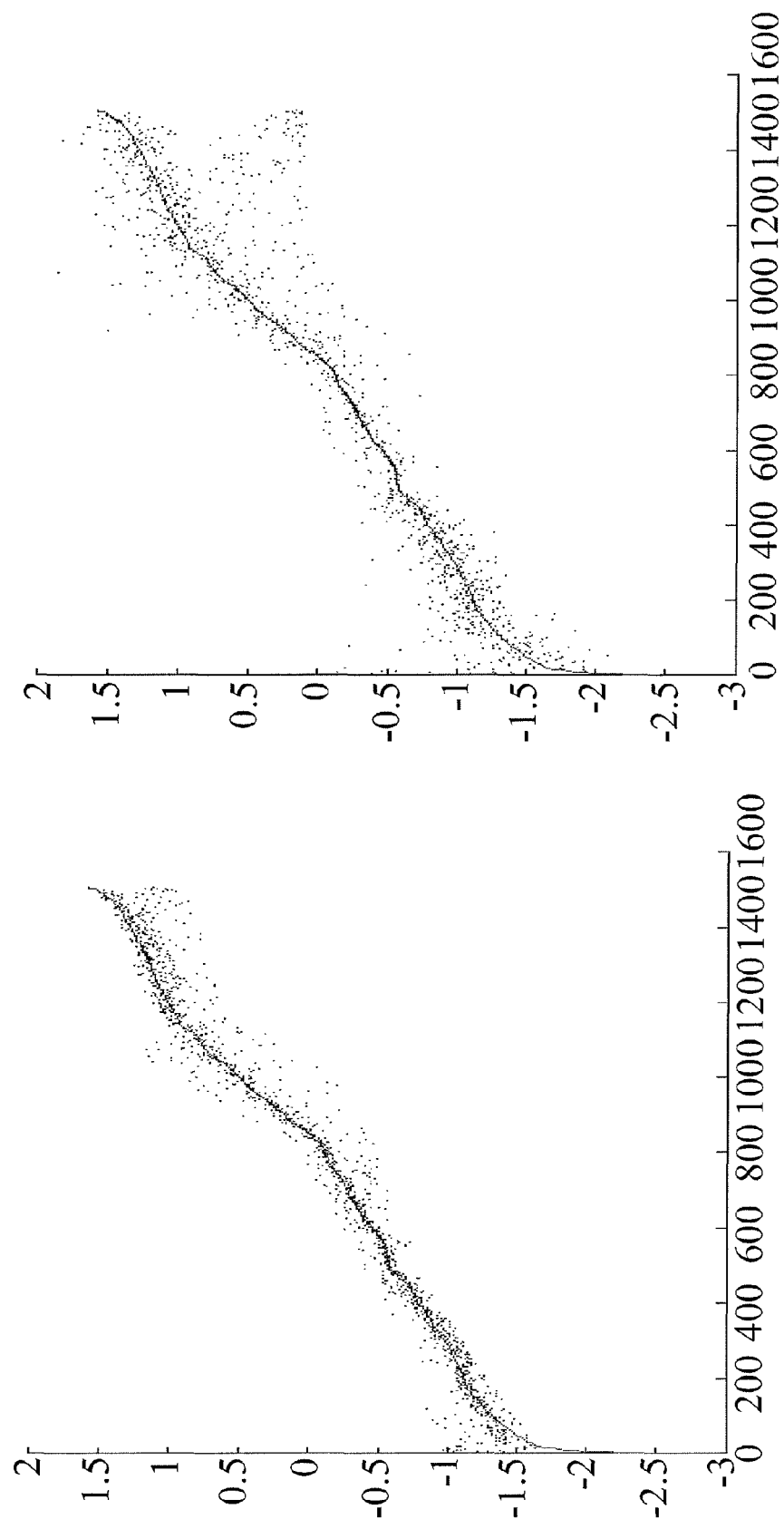

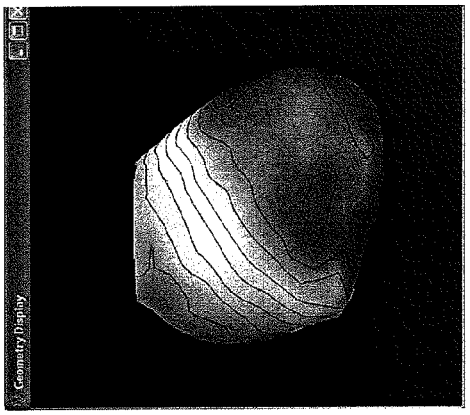
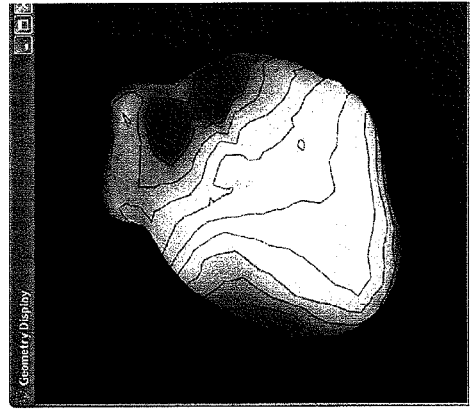
Fig. 14C
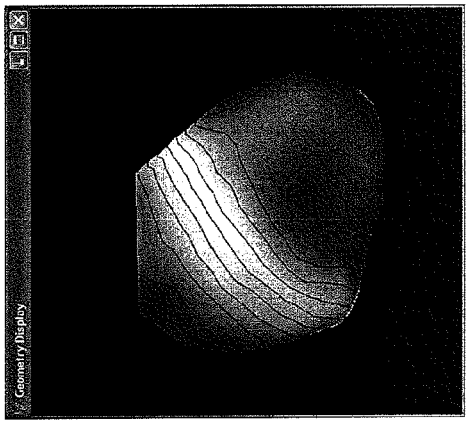
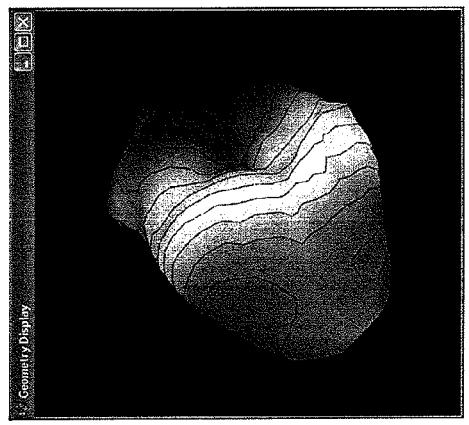
Fig. 14B
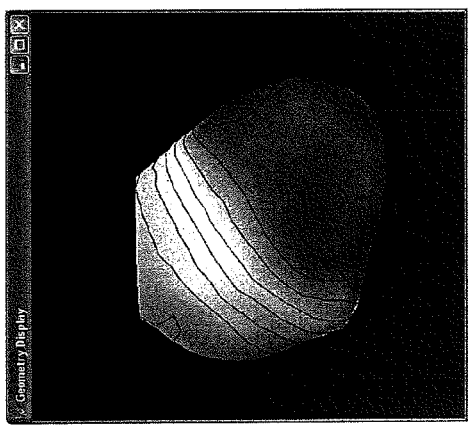
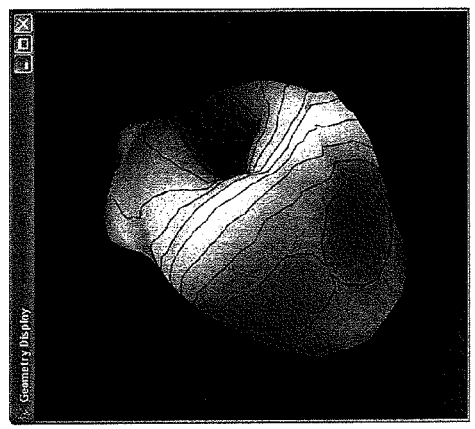
Fig. 14A

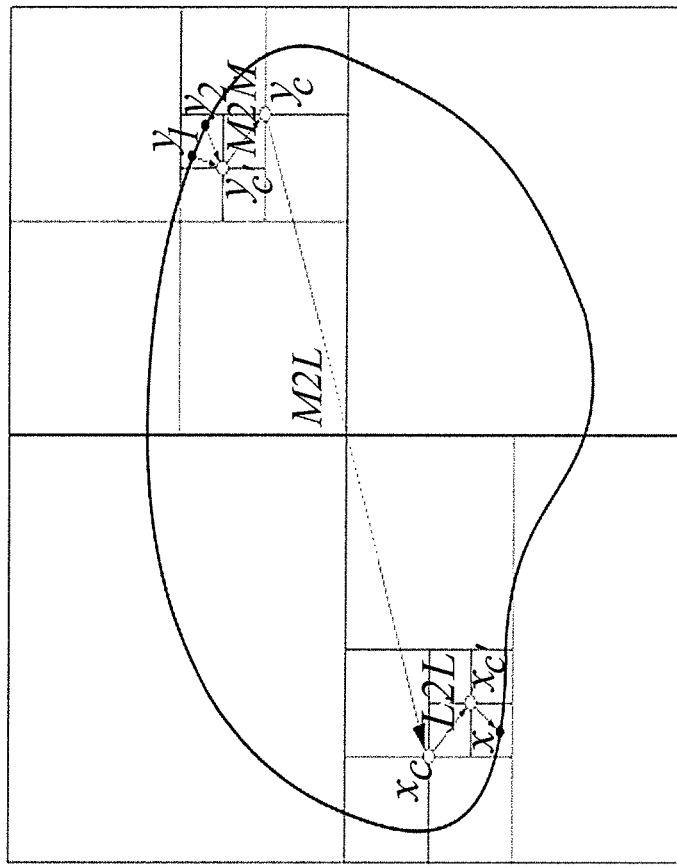
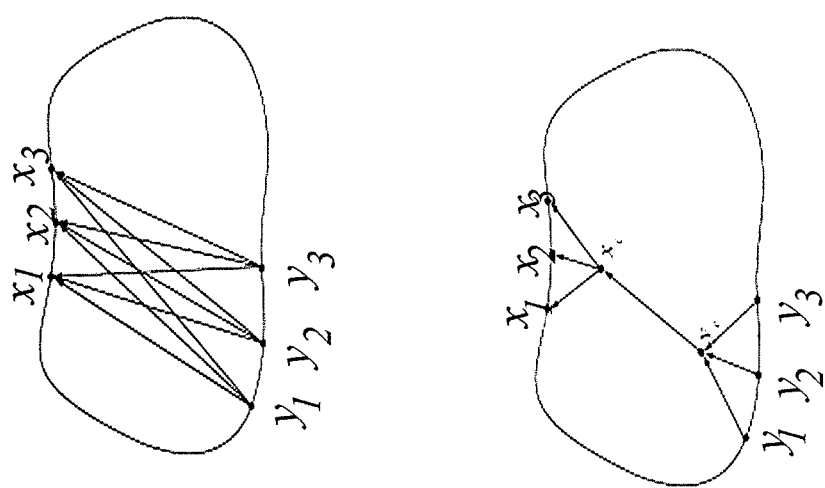
Fig. 15

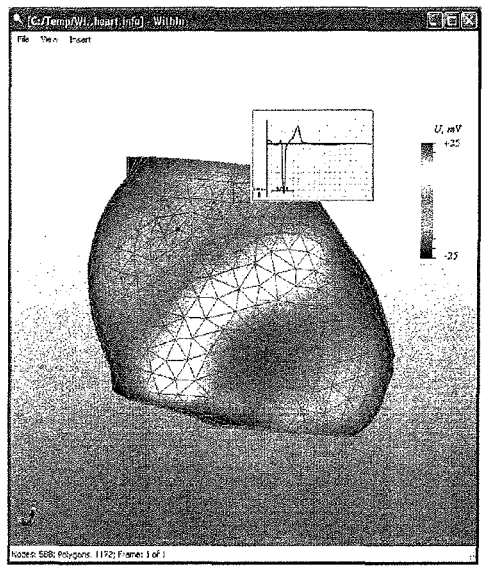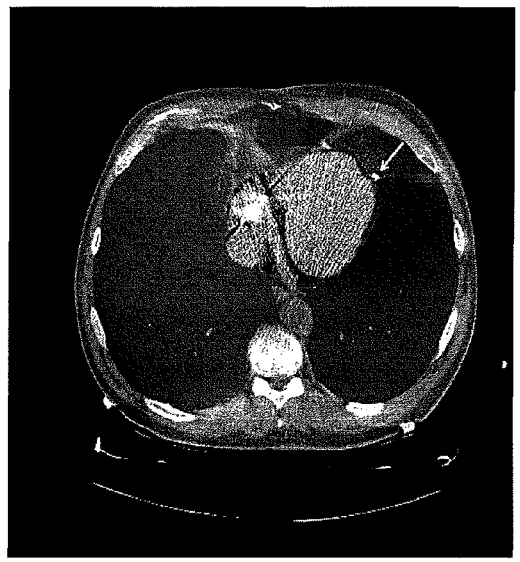
Fig. 16A     Fig. 16B
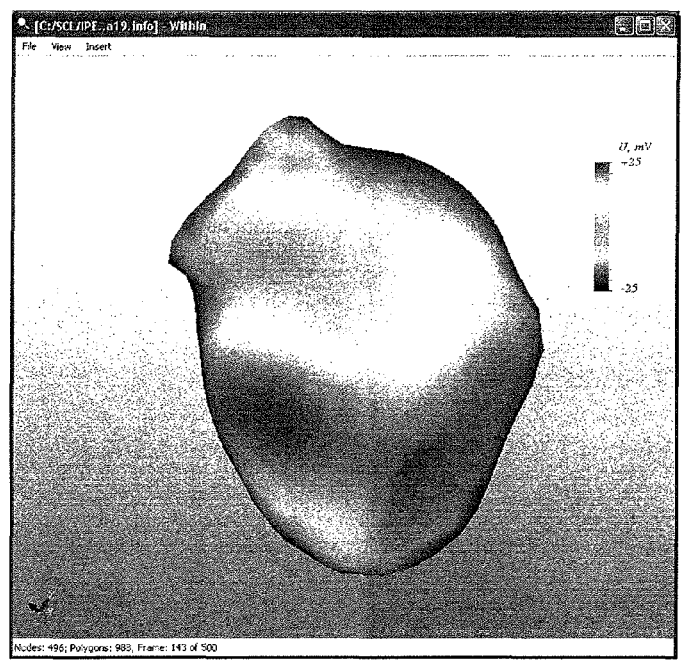
Fig. 16C

METHOD OF NONINVASIVE ELECTROPHYSIOLOGICAL STUDY OF THE HEART

FIELD OF THE INVENTION

The invention relates to medicine, namely to cardiology, cardiovascular surgery and functional diagnosis (clinical physiology), and is intended for performing a diagnosis procedure such as noninvasive electrophysiological study of the heart. More specifically, the invention is intended for reconstructing the dynamics (propagation) of the heart electric field at internal points of the chest and, more particularly, for obtaining intraesophageal and epicardial electrograms, as well as for performing an activation epicardial mapping, namely for obtaining epicardial isopotential and isochronous maps (myocardium activation patterns) by a noninvasive way, i.e., without inserting registration devices into heart chambers, pericardial cavity, esophageal cavity, etc.

BACKGROUND OF THE INVENTION

The most common method for diagnosis of cardiac electrophysiological processes routinely used in clinical practice is electrocardiography in 12 standard leads. Simplicity and low cost of the standard electrocardiographical study together with its relatively high informativity have lead to its extremely widespread use in the daily practice.

However, the electrocardiographical method has principled limitations. Activity of certain compartments of the myocardium is inadequately reflected in electrocardiographical signals registered in standard leads. As an example, difficulties in ECG-diagnosis of myocardial infarction of back-basal compartments of the left ventricle may be named. Furthermore, according to the superposition principle of electrodynamics, any electrocardiogram is the sum of electric potentials coming from sources at a great number of myocardium points. Since electrophysiological processes in different areas of the cardiac muscle proceed simultaneously, it is rather difficult to determine a local electric activity of the myocardium on standard ECG-leads. For example, an atrial re-polarization wave in humans in conditions of a normal cardiac rhythm is not revealed in ECG, as it is "hidden" by a high-amplitude QRS-complex reflecting a ventricular depolarization. The vector-electrocardiography technique is characterized by the same limitations.

Greater possibilities are provided by a method for surface electrocardiographical mapping of the chest. The method consists in a synchronic registration of multiple (from 40 to 250 and more) unipolar ECG-leads from the chest surface and in constructing maps of the electric potential distribution over the chest surface by interpolation for each discrete moment of the cardiocycle.

However, this method does not allow one to determine more precisely a local electric activity of the myocardium. If an electrode is located on the chest surface, contributions to ECG-signal from the nearest and most remote, regarding a registration electrode, segments of the myocardium differ from each other by approximately one order. For an electrode placed on the heart surface this difference is three orders. In this connection, for revealing a local electric activity of the heart, methods of invasive ECG registration are used with an attempt to bring electrodes closely to the heart surface as much as possible.

Transesophageal electrophysiological study of the heart is based on inserting a probe with registration electrodes into the esophagus cavity. The esophagus at its certain part adjoins close enough to posterior wall of the left atrium and to posterior wall of the left ventricle; therefore, intraesophageal ECG-signals selectively register the activity of these heart compartments. Intraesophageal electrocardiography is applied, in particular, for differential diagnosis of supraventricular and ventricular arrhythmias (Transesophageal electrostimulation of the heart (Under edit. Sulimov V. A., Makolkin V. I.). Moscow: Meditsina, 2001.—208 pp. [in Russian]).

For the same purposes in conditions of reanimation and intensive therapy departments, ECG-registration from the vena supra-cava via postclavicular catheter is used. The role of an electrode plays the column of saline solution within catheter. According to this technique, an activity of the right atrium is mainly registered (Kalinin V. V. Application of ECG recorded through postclavicular catheter for differential diagnosis of supraventricular arrhythmias.—Proceedings of V Session of MNOAR. Moscow: 2005 [in Russian]).

However, methods above-mentioned permit one to reveal a local electric activity only of individual structures of the heart.

For a complex evaluation of cardiac electrophysiological processes and topical diagnosis of cardiac rhythm disturbances, an invasive electrophysiological study of the heart based on the direct registration of a set of electrocardiograms from epicardial or endocardial surfaces of the heart is carried out. These methods may be applied on "open-heart" in conditions of thoracotomy, as well as on the basis of intervention technologies of inserting registration devices (catheters) into cardiac cavities by transvascular access or into pericardial cavity by its fluoroscopically-guided transskin puncture.

Up-to-date realizations of methods above-mentioned are directed to a precise determination of three-dimensional (3-D) coordinates of registration electrodes by non-fluoroscopic techniques and to a visualization of results in the form of isopotential and isochronous maps on models of heart compartments with means of computer graphics. Computer models of heart compartments are constructed at a great number of electrogram-registration points with known coordinates, as well as on the basis of CT or MRT data of the heart (Revishvili A. Sh., Rzaev F. G., Djetybaeva S. K. Electrophysiological diagnosis and intervention treatment of complicated forms of heart rhythm disturbances with using a system of three-dimensional electro-anatomical mapping.—Vestn. Aritmol. 2004, 34: 32-37 [in Russian]; Pokushalov E. A., Turov A. N., Shugaev P. L., Artemenko S. L. Radiofrequency ablation of ventricular tachycardia by transpericardial approach.—Vestn. Aritmol. 2006, 44: 58-62 [in Russian]).

To this group of methods, one can also refer methods for non-contact endocardial mapping based on inserting a "swimming" balloon catheter into cardiac cavities, registering a set of electrograms on the heart surface and reconstructing endocardial electrograms by computational way on data obtained (Schilling R. J., Kadish A. H., Peters N. S. et al. Endocardial mapping of atrial fibrillation in the human right atrium using a non-contact catheter.—European Heart Journal. 2000, 21: 550-564).

The drawback of methods above-disclosed which is avoided in the present invention is their invasive character.

Analogues of the present invention are methods for electrogram reconstructing at internal points of the chest by computational way according to the data of synchronic registration of ECG sets on the chest surface.

These methods are based on solution of the inverse problem of electrocardiography. The statement of the inverse problem of electrocardiography (IP ECG) is formulated in works of Barr D., Spach M. Solutions of the inverse problem directly expressed in terms of potentials//Theoretical fundamentals of electrocardiology [Russian translation under edit. Nelson K. V. and Geselovitz D. V.]—Moscow: Meditsina 1979, pp. 341-352; MacLeod R. S., Brooks D. H. Recent progress in the inverse problem in electrocardiology//IEEE Eng. in Med. Bio. Mag. 17:1, pp. 78-83, January 1998; Rudy Y., Messinger-Rapport B. J. The inverse problem in electrocardiography: Solutions in terms of epicardial potentials. CRC Crit. Rev. Biomed. Eng. 1988, 16: 216-268.

From the mathematical standpoint, IP ECG is a problem of harmonic continuation of the potential in the direction of sources, i.e., the Cauchy problem for the Laplace equation. Computational domain, in which the Laplace equation is defined, represents a part of the chest bounded by heart external surface, chest surface on which ECG-registration is accessible, and by imaginary cross-sections of the chest at the level of the diaphragm and clavicles.

At that part of the chest surface where ECG-registration is accessible, values of the electric potential obtained as a result of ECG-mapping, as well as the condition of equality-to-zero of a potential normal derivative are given. These data compose the Cauchy conditions.

The Cauchy problem consists in finding the electric field potential in indicated domain and its trace on the heart surface and on cross-sections of the chest in such a way that the potential in computational domain would satisfy the Laplace equation, while on the torso surface where ECG-registration is accessible it would satisfy the Cauchy conditions.

According to Hadamard, the Cauchy problem for the Laplace equation is ill-posed, as any negligible errors in the condition may result in arbitrary large errors in the solution. For solving the Cauchy problem for the Laplace equation, it is necessary to apply special so-called regularizing algorithms of solution (Denisov A. M. Introduction to the theory of inverse problems [in Russian].—Moscow: Moscow State University, 1994; Tikhonov A. N., Arsenin V. Ya. Methods for solution of incorrect problems [in Russian].—Moscow: Nauka, 1986, 312 pp.).

To solve the Cauchy problem for the Laplace equation in above-disclosed statement (the inverse problem of electrocardiography) by an analytical way appears to be impossible. Therefore, the inverse problem of electrocardiography is numerically solved by means of computational mathematics with using computer techniques.

The specific way to solve the inverse problem of electrocardiography, besides aspects associated with surface ECG-mapping, defines a method for determination and representation in a "numerical form" of heart and torso boundary surfaces;

an algorithm of numerical solution of the problem.

One of the ways for solving the inverse problem of electrocardiography is a method for reconstructing the electric field on "quasi-epicard", i.e., on a conditional spherical surface surrounding the heart. From the mathematical standpoint, this method is based on representation of the heart electric field potential in the form of a harmonic polynomial (sphere function) whose coefficients are found from the condition of equality (or the minimum of mean square deviation) of values of polynomial and values of an ECG-signal at points of its registration with taking into account the equality-to-zero of a potential normal derivative on the chest surface. For providing the stability of solution, polynomial of degree not higher than 4 is used. The essential disadvantage of this method is that, when the radius of sphere diminishes, i.e., as "quasi-epicard" surface approximates to a real surface of the heart, the accuracy of potential reconstructing sharply drops. When "quasi-epicard" surface approximates to the chest surface, the resolution of the method in terms of revealing a local electric activity of the myocardium decreases (Titomir L. I., Kneppo P. Mathematical modeling of heart's bioelectric generator.—Moscow: Nauka, Physmathlit, 1999.—448 pp. [in Russian]; Titomir L. I., Trunov V. G., Aidu E. A. I. Noninvasive electrocardiography.—Moscow: Nauka, 2003.—198 pp. [in Russian]).

In order to solve boundary problems for the Laplace equation, methods of integral equations of the potential theory, more known in English-written literature as boundary element methods, are widely used (Brebbia C., Telles J., Wrobel L. Boundary element methods [Russian translation].—Moscow, Mir, 1987). The present approach to IP ECG solution is proposed in works of Taccardi E., Plonzi R., Barr R. (Barr R., Spach M Inverse problem solutions directly expressed in terms of a potential//Theoretical fundamentals of electrocardiography [Russian translation]. The above-mentioned methods suppose, in particular, the representation of heart and torso surfaces as polygonal surfaces, i.e., splitting boundary surfaces into a great number of triangular elements. According to the boundary element method, IP ECG for a homogeneous model of the chest is reduced to solving a system of two Fredholm integral equations of $1^{st}$ and $2^{nd}$ kinds, which is approximately substituted by a system of matrix-vector equations:

$$A_{11}x + A_{12}y = c_1,$$

$$A_{11}x + A_{22}y = c_2 \quad (1)$$

where $A_{i,j}$ are known matrices; $x_1, x_2$ are unknown vectors having a sense of sought-for values of the potential and its normal derivatives in nodes of triangulation grids approximating the heart surface and torso cross-section surfaces; $c_1$, $c_2$ are known vectors calculated on known data of the problem.

In the method of noninvasive epicardial mapping suggested by Shakin V. V. et al. the following algorithm of IP ECG solution was used.

The system of matrix-vector equations (1) by means of elementary transformations was reduced to a system of linear algebraic equations (SLAE) to be resolved in explicit form:

$$\Phi_H = Z_{HB} \cdot \Phi_B, \quad (2)$$

where $\Phi_H$ is an unknown vector having a sense of sought-for values of the potential and its normal derivatives in nodes of triangulation grids approximating the heart surface and torso cross-section surfaces; $Z_{HB}$ is a known matrix; $\Phi_B$ is a known vector. For computing matrix $Z_{HB}$, it is necessary to use an inversion procedure of matrices entering the system (1), one of matrices to be inversed being non-square and ill-conditioned. For implementation of this procedure, constructing a Moore-Penrose pseudo-inverse matrix on the basis of SVD-decomposition of an initial matrix and substituting small singular values by zeroes were performed.

Heart and torso surfaces were represented as simplified models in the form of cylindrical and ellipsoidal surfaces to be constructed on the basis of two-projection roentgenography of the chest. Results of mapping in the form of isopotential and isochronous maps were imposed on model scanned-schemes of heart compartments. This methodology was used for revealing a localization of additional pathways (APW) at manifested WPW syndrome and ectopic sources at ventricular extrasystole (Shakin V. V. Computational electrocardiography [in Russian].—Moscow: Nauka, 1980).

In his works, Shakin V. V. has emphasized a promising outlook of the application of computed tomography techniques for more precise constructing the torso and heart surfaces; however, this approach could not be used because of unsatisfactory development of methods for computer tomography of the heart.

The most similar to a method claimed here (prototype) is the methodology of noninvasive electrocardiographic imaging (ECGI).

In this methodology, a surface mapping is performed with using 240 unipolar electrodes placed in a special vest to be put on a patient for a study period. The torso and heart surfaces are determined on the basis of computer (CT) or magneto-resonance (MRT) tomography of the chest. A reconstruction algorithm is based on solution of the inverse problem of electrocardiography with using the boundary element method.

The torso and heart surfaces are approximately represented as polygonal surfaces. For solving IP ECG, the system of matrix-vector equations (1) is also used, which is reduced to a system of linear algebraic equations by elementary transformations $$Ax=c \quad (3)$$

where x is an unknown vector having a sense of sought-for values of the potential in nodes of triangulation grids approximating the heart surface and torso cross-section surfaces; A is a known matrix; c is a known vector.

The system of linear algebraic equations (3) is ill-conditioned. For its solving the Tikhonov regularization method and the iterative regularization method based on GMRes-algorithm are applied. The Tikhonov method is based on solution of the following system instead of the system (3):

$$(A^T \cdot A + \alpha E)x = A^T c,$$

where $A^T$ is a matrix transponated in respect of matrix A; E is a unit matrix; $\alpha$ is a regularization parameter (a small positive real number).

The iterative regularization method is based on solution of the system (3) by a method of sequential approximations with restricting a number of iterations on the basis of GMRes-algorithm; this method belongs to a group of Krylov subspace methods (Ramanathan C., Ghanem R. N., Jia P., Ryu K., Rudy Y. Electrocardiographic Imaging (ECGI): A Noninvasive Imaging Modality for Cardiac Electrophysiology and Arrhythmia//Nature Medicine, 2004; 10: 422-428; Rudy Y., Ramanathan, C., R. N. Ghanem, R. N., Jia P. System and Method For Noninvasive Electrocardiographic Imaging (ECGI) Using Generalized Minimum Residual (GMRes)// U.S. Pat. No. 7,016,719 B2, 2006).

The similar technique was used in works of Berger T, Fisher G., Pfeifer B. et al. Single-Beat Noninvasive Imaging of Cardiac Electrophysiology of Ventricular Pre-Excitation// J. Am. Coll. Cardiol., 2006; 48: 2045-2052.

This technique was applied for revealing APW-localization at manifested WPW syndrome, ectopic sources at ventricular extrasystole and tachycardia, reconstruction of the dynamics of myocardium activation at atrium flutter.

Application of the boundary element method for solving IP ECG is rather promising, in particular, in connection with that a representation of boundary conditions containing normal derivatives and a computation of normal derivatives of solution at boundary surfaces do not require numerical differentiation. However, methods above-considered have a number of disadvantages associated with specific character of the boundary element method.

The accuracy of approximating a system of boundary integral equations to a system of matrix equations directly depends on a number of elements of a boundary-element grid, as well as is rather sensitive to the quality of grid constructing. In the boundary element method a matrix of final SLAE turns out to be filled. Inversion of matrices with such structure requires considerable computational resources. In this connection, at the current level of development of mass computer techniques it is to be used matrices of a relatively not high size, i.e., to be confined by grids with a relatively small ($1 \cdot 10^3$-$5 \cdot 10^3$) number of elements. This circumstance puts limitations on the accuracy of solving IP ECG. A high demand of the boundary element method to the quality of grids considerably complicates a problem of automatic constructing grids on CT or MRT data.

Above-considered difficulties which already take place, when solving IP ECG for a homogeneous model of the chest, are still more growing when one makes an attempt to take into account an electrical inhomogeneity of chest tissues.

Solution of the inverse problem of electrocardiography by the boundary element method for a model of the chest with a variable coefficient of electroconductivity encounters serious mathematical difficulties.

When solving the inverse problem of electrocardiography by the boundary element method for a model of the chest with a piecewise-constant coefficient of electroconductivity, a system of 2N+1 matrix-vector equations arises, wherein N is a number of regions with different electroconductivity. Direct concatenation of a block matrix of this system in a united matrix leads to the formation of the matrix of great size with a high conditionality number. For its inversion, considerable computational resources (memory, computer fast-action) are required, and it cannot be implemented with satisfactory accuracy. Reducing a system of matrix-vector equations to a system of linear algebraic equations regarding an unknown vector of potentials by the rearrangement of a block matrix to a diagonal form requires a great number of matrix algebraic operations and, therefore, is also distinguished by low accuracy and by the necessity in considerable computational resources.

The present invention is aimed at overcoming above-mentioned disadvantages.

SUMMARY OF THE INVENTION

For carrying out an electrophysiological study of the heart, a registration of a set of electrograms from the heart surface is necessary, based on which isopotential, isochronous maps are constructed and electrophysiological processes in the cardiac muscle are diagnosed. For obtaining these electrograms, an invasive way, i.e., an insertion of special registration devices into heart chambers or pericardial cavity, is used.

The present invention consists in reconstructing electrograms, whose experimental registration requires an invasive access, by computational way on unipolar ECG recorded at 80 and more points of the chest surface. Based on a set of surface electrograms for each discrete moment of the cardiocycle, values of the heart electric field potential at points of ECG-recording are determined and, by interpolation, a value of the electric field potential at each point of the chest surface is calculated. On data of any visualization methodology (computer tomography, MRT) boundaries of the chest surface and heart epicardial surface are determined.

Further, a harmonic continuation of the electric field potential throughout the whole surface of the chest up to the heart epicardial surface is implemented by computational way on the basis of solution of the Cauchy problem for the Laplace equation in a homogeneous medium. For solving the Cauchy problem for the Laplace equation, the boundary element method is applied; on its basis an initial problem is reduced to a problem of solving a system of matrix-vector equations. For improving the accuracy of the method, an iteration algorithm of solution of a system of matrix-vector equations is used. At each step of an iteration procedure, a system of linear algebraic equations is solved on the basis of regularizing algorithms. For performing an operation of matrix-vector multiplication, the "fast multipole method" is applied, which allows one to significantly increase the rate of calculations for matrices of high size.

The above-written sequence of procedures is repeated for each discrete moment of the cardiocycle. On obtained values of the potential at given internal points of the chest, required electrograms are reconstructed by interpolation. Based on reconstructed electrograms, isopotential, isochronous maps on realistic models of the heart are constructed, the dynamics of the myocardium excitation is reconstructed and diagnosis of electrophysiological processes in the cardiac muscle is performed.

BRIEF DESCRIPTION OF FIGURES

FIG. 5 illustrates processing of ECG signals in the course of ECG mapping in real-time mode. In upper drawing, power-line noises are shown, in lower one—muscle noises.

FIG. 5 (continued). In upper drawing, an isoline drift is shown, in lower one—the resulting filtered signal.

FIG. 8 illustrates constructing polygonal surfaces (triangulation grids) of the torso and heart on the basis of voxel models. In the left column, stages of constructing a polygonal grid of the heart are shown: an initial grid (350 000 elements), a reconstructed grid (20 000 elements) and a rarefied grid (3 000 elements). In the right column, stages of constructing a polygonal grid of the torso are shown: an initial grid (900 000 elements), a reconstructed grid (20 000 elements) and a rarefied grid (3 000 elements).

FIG. 9 shows an automatic determination of coordinates of electrodes on CT or MRT data of the chest.

FIG. 12 shows convergence diagrams of an iterative procedure for different methods of choice of a regularization parameter. In upper drawing, an algorithm convergence is shown without verifying the accuracy of a regularization parameter α at each step of an iterative procedure. In lower drawing, an algorithm convergence is shown with verifying the accuracy of a regularization parameter α at each step of an iterative procedure.

FIGS. 13 and 14 give results of electric field reconstructing on the heart surface based on the aforesaid algorithm and method disclosed in US patent (Rudy Y., Ramanathan C., Ghanem R. N., Jia P. System and method for noninvasive electrocardiographic imaging (ECGI) using generalized minimum residual (GMRES)//U.S. Pat. No. 7,016,719 B2, 2006).

FIG. 15 (continued) compares the running time for classical algorithm BEM and for FMM BEM.

DETAILED DESCRIPTION OF PREFERRED EMBODIMENTS

To provide a comprehensive understanding of the invention, its specific illustrative embodiments are described below; however, those of ordinary skill in the art will recognize that methods and systems may be modified within the scope of the invention as defined by the appended claims.

Methods and systems disclosed here use a device of surface ECG mapping, visualization techniques for CT or MRT, computing techniques, as well as mathematical algorithms of solution of the inverse problem of electrocardiography for noninvasive reconstructing electrograms at internal points of the chest and on heart epicardial surface and for constructing isopotential and isochronous epicardial maps on a realistic three-dimensional (3-D) computer model of the heart.

Figure 1:
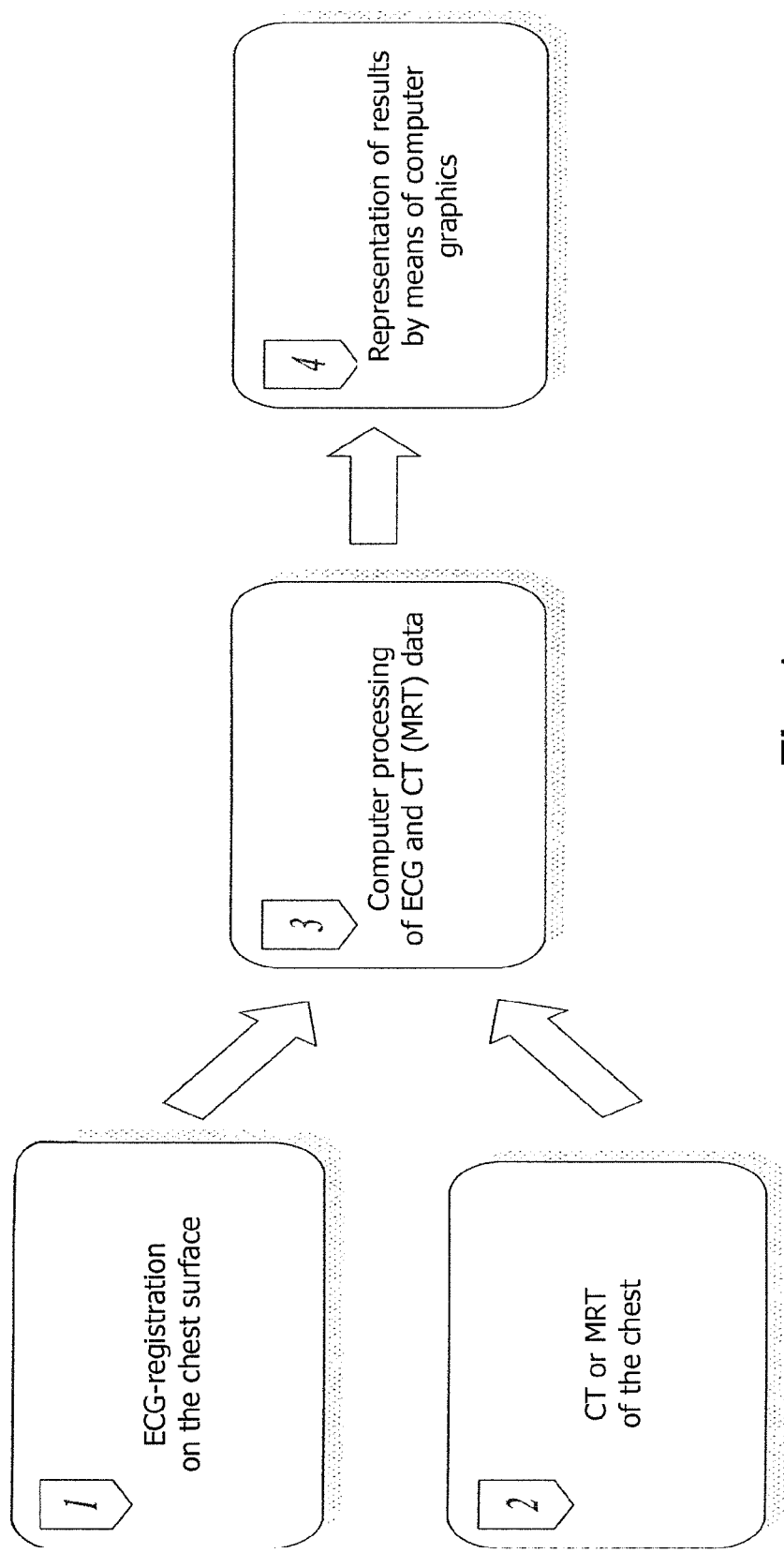
FIG. 1 illustrates a general scheme of the method.

FIG. 1 illustrates a general schematic view of the method. The method includes (1) a registration of 240 unipolar ECG on the chest surface, (2) an implementation of CT or MRT of the chest, (3) data processing of surface ECG mapping and of computer (CT) tomography using computing techniques and (4) a representation of the obtained electrophysiological information with using means of computer graphics.

Figure 2:
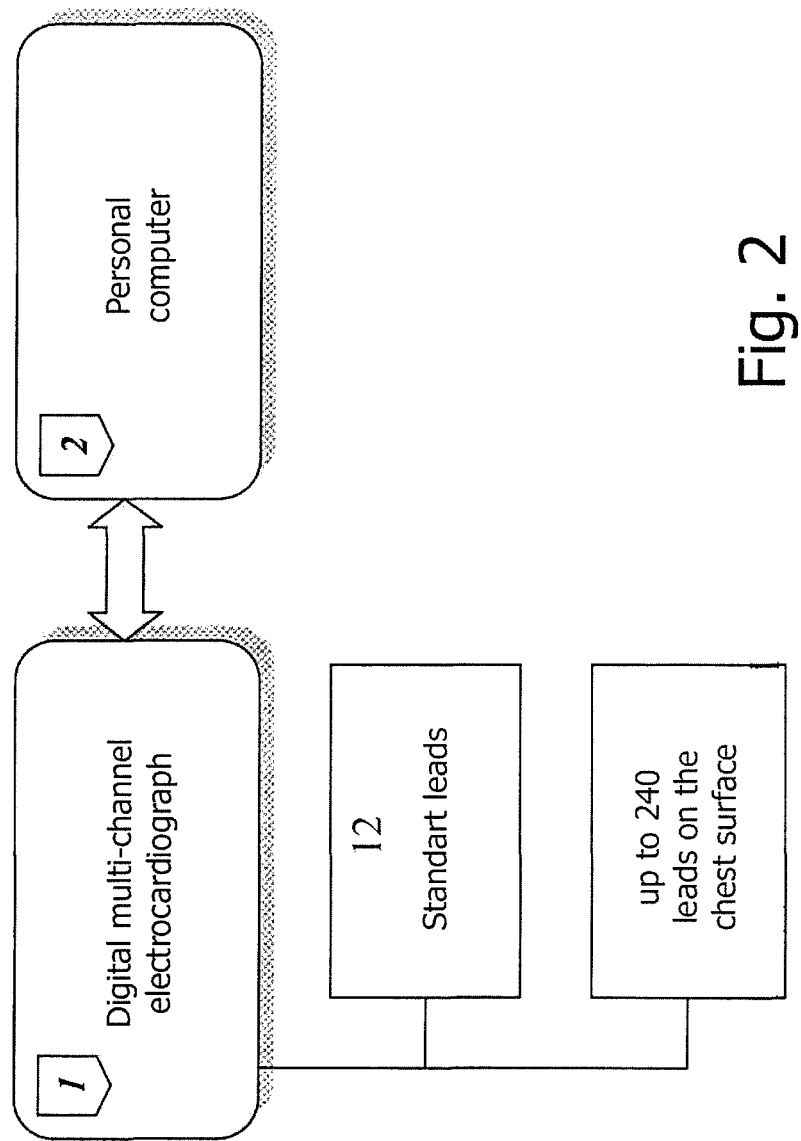
FIG. 2 shows a schematic view of the methodology of surface ECG mapping.

FIG. 2 illustrates a schematic view of the methodology of surface ECG mapping. A mapping device comprises a digital multi-channel electrocardiograph (1) connected with a personal computer (2). The digital multi-channel electrocardiograph allows one to register ECG-signals in 12 standard leads and in up to 240 unipolar leads from the chest surface.

Figure 3:
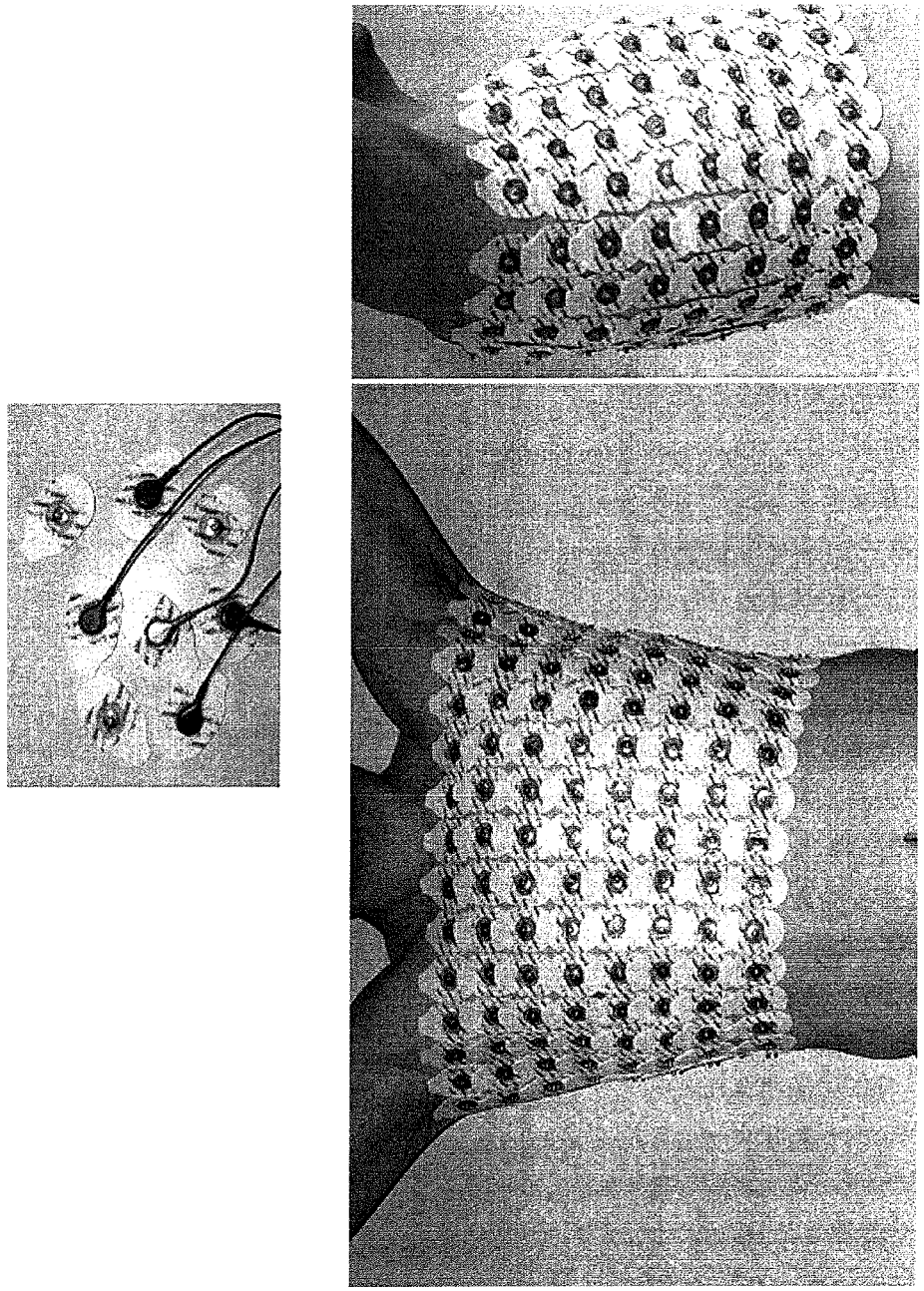
FIG. 3 illustrates a scheme of imposing electrodes on the chest surface.

FIG. 3 illustrates a scheme of imposing electrodes. For surface ECG mapping one-off chlorine-silver electrodes are used (1). Electrodes are applied in the form of 8 horizontal belts positioned at similar distances along the vertical. The first belt is positioned at the level of sterno-cleidal articulation, the $8^{th}$ one—at the level of lower edge of rib-arch. Each belt includes 30 electrodes placed at similar distances in circumference of the chest (2).

Figure 4:
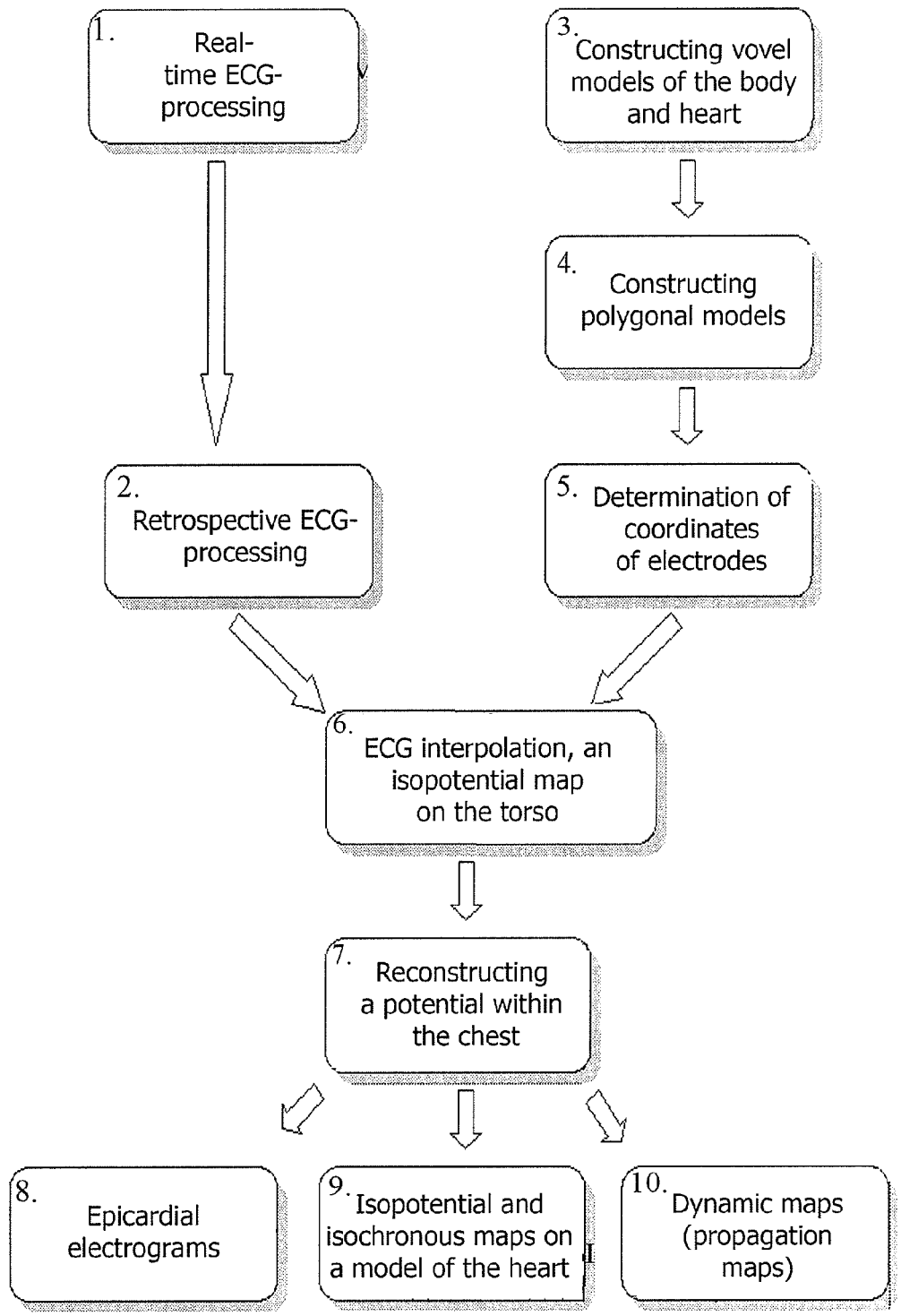
FIG. 4 presents the main stages of computer processing of the information.

FIG. 4 depicts the main stages of computer processing of the information. The stage (1) is a real-time processing of ECG-signals in the course of multi-channel ECG registration from the chest surface. The stage (2) is a retrospective processing of ECG-signals. The stage (3) includes constructing voxel models of the chest, heart and its compartments on CT or MRT data. The stage (4) comprises constructing polygonal surfaces of the chest, heart and its compartments. The stage (5) includes an automatic determination of coordinates of registration electrodes on the chest surface according to CT or MRT data. At stage (6) a surface interpolation of values of surface mapping ECG-signals at each discrete moment and a construction of isopotential maps on the chest surface are performed. The stage (7) comprises a computational reconstruction of the heart electric field potential at internal points of the chest and on heart epicardial surface. At the last stage, reconstructing epicardial electrograms (8) and constructing epicardial isopotential, isochronous maps with using means of computer graphics (9) on a realistic computer model of the heart and visualizing the dynamics of electrophysiological processes of the myocardium in animation mode (propagation mapping) (10) are performed, respectively.

FIG. 5 illustrates processing of ECG-signals in the course of real-time ECG mapping. ECG-signals registered are reflected in computer display. An operator controls the quality of an ECG-signal in each of the leads; if necessary, a programmed suppression of power-line (1) и muscle (2) noises and of isoline-drift (3) is applied. Automatic control of the contact of an electrode with skin and correctness of imposing electrodes are also carried out based on spectral and mutual-correlation analyses of ECG-signals. Results obtained in stage (1) are digitalized and filtered values of ECG-signals in 240 unipolar leads from the chest surface and in 12 standard leads with the duration up to 3 minutes.

Figure 6:
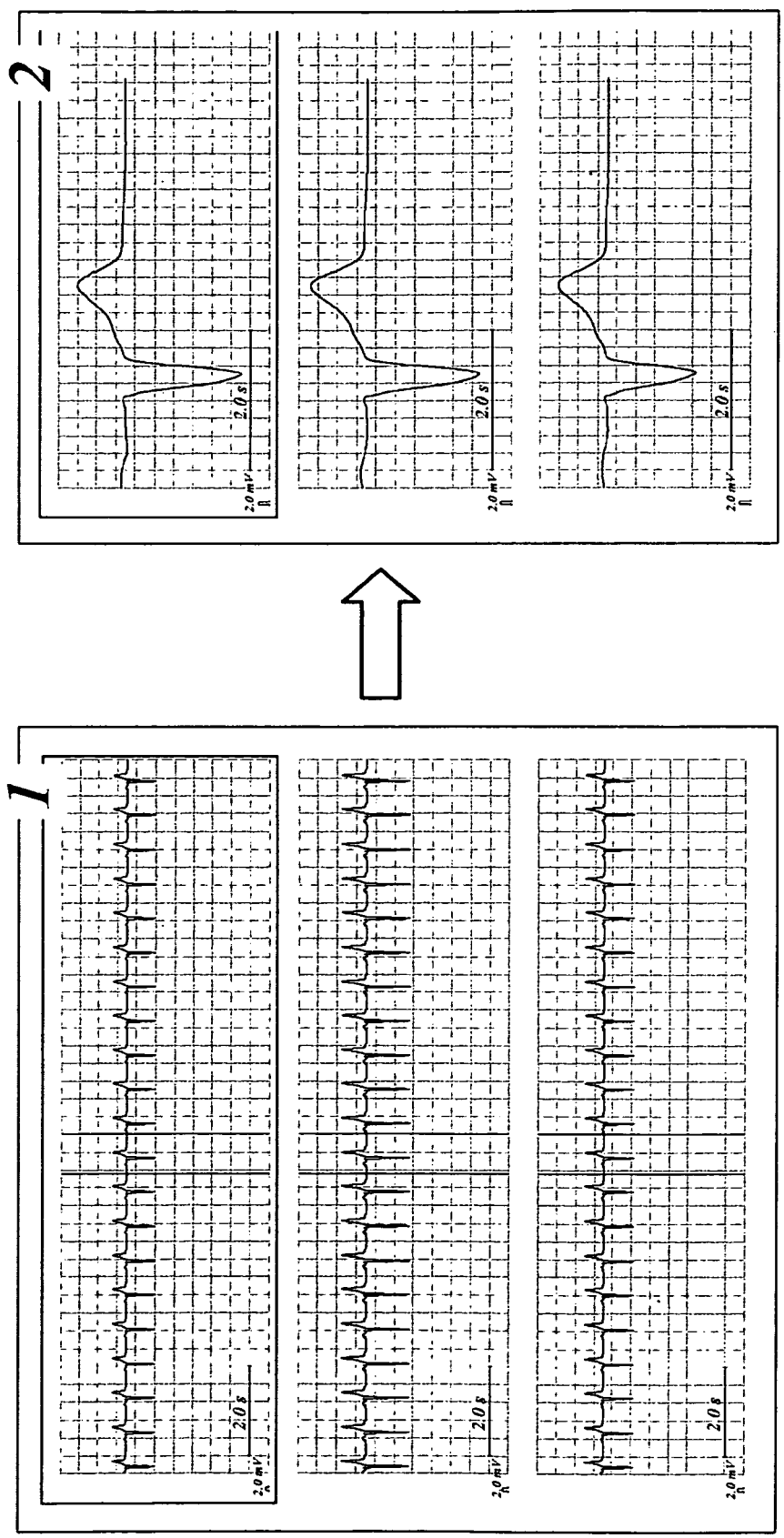
FIG. 6 illustrates a retrospective processing of ECG-signals.
Figure 6:
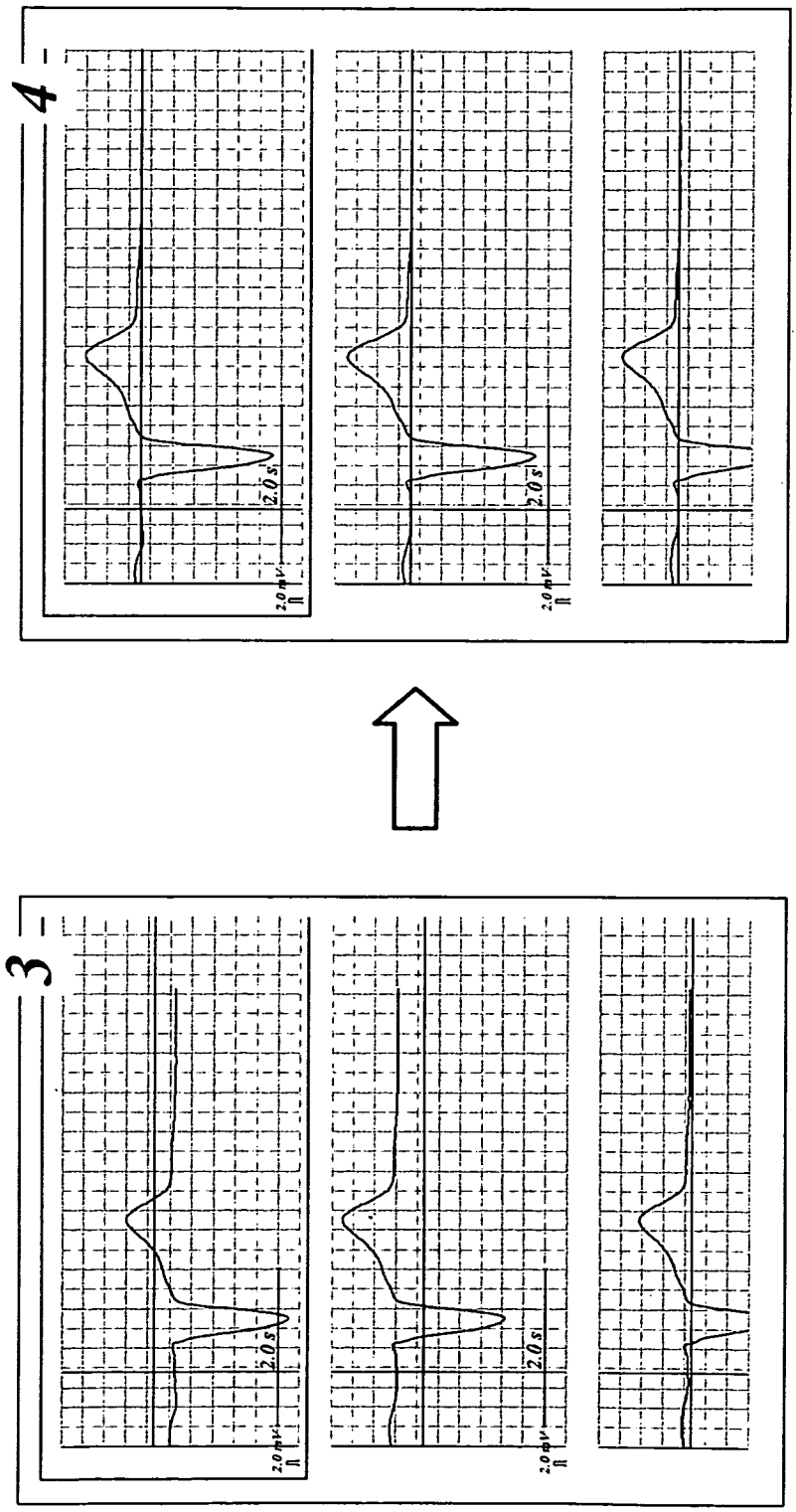

FIG. 6 depicts a retrospective processing of ECG-signals.

An operator looks through ECG-signals registered and selects one or several cardiocycles for posterior processing (1,2). Further, a reduction of ECG to a united isoline (3, 4) is implemented: to this end, operator in one of ECGs selects such a time interval r, within which an ECG-signal coincides with an isoline (as a rule, this interval belongs to the segment PQ). Correction of ECG signals is implemented according to the formula:

$$U_0(t)=U(t)-u_0,$$

where $U_0$ (t) is the corrigiert ECG-signal, U(t) is an initial ECG-signal, $u_0$ is an averaged value of initial ECG-signal within a time interval τ.

Afterwards, an operator selects a fragment under interest of the cardiocycle for subsequent calculations.

Figure 7:
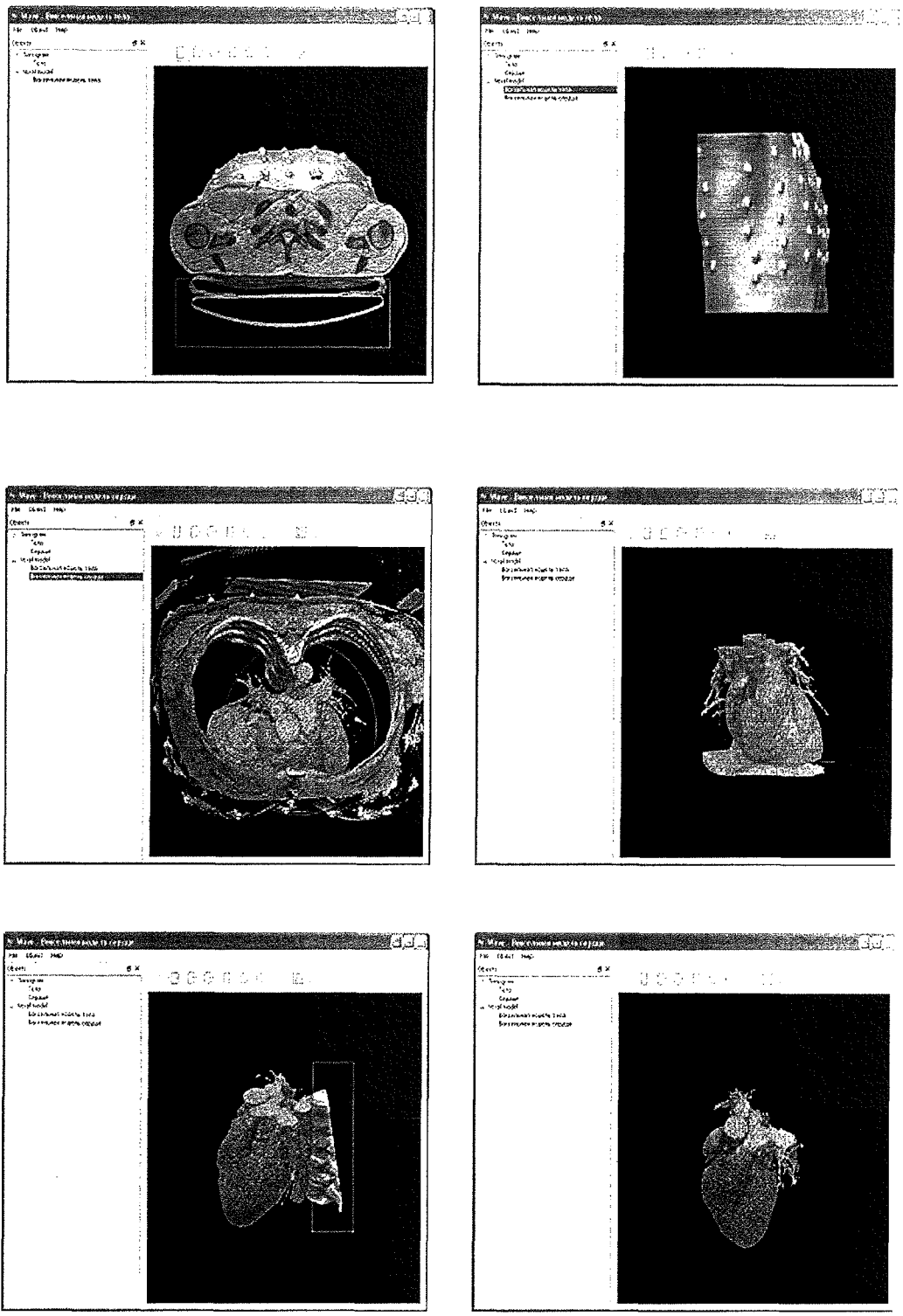
FIG. 7 shows constructing a voxel model of the torso and heart in voxel graphics editor.

FIG. 7 illustrates constructing a voxel model of the torso and heart in voxel graphics editor.

On CT or MRT data of the chest and heart, a voxel rendering of anatomical structures of the chest is realized. To this end, a "shear-warp factorization" of the viewing transformation algorithm, which belongs to a group of scanline-order volume rendering methods, is used.

The concept of voxel rendering method applied here consists of three main steps (Philippe Lacroute Fast Volume Rendering Using a Shear-Warp Factorization of the Viewing Transformation.—Ph.D. dissertation, Technical Report CSL-TR-95-678, Stanford University, 1995).

At first step, volume data are transformed by a shear matrix in the corresponding object space, each parallel slice of volume data after transformation passing through a special filter for diminishing distortions.

At second step, an intermediate 2D image within the same shear space is formed from a combined set of filtered and sheared slices by its direct-order superposition.

At third step, the intermediate 2D image obtained is transferred into a normal image space with using a shear matrix and, further, it again passes through a filter for forming a final image.

An operator with the help of instruments of voxel edition makes ready a voxel model of the torso, heart or one of its structures.

FIG. 8 illustrates constructing polygonal surfaces (triangulation grids) of the torso and heart on the basis of voxel models.

Based on obtained voxel models, polygonal surfaces consisting of united plane triangles are automatically constructed. Initial data represent a three-dimensional scalar field of densities in a voxel presentation, i.e., a three-dimensional right-angled grid, in whose nodes values of conditional densities of chest tissues are given. Constructing triangulation grids of the torso and heart represents a construction of polygonal surfaces which by the nearest way repeat the surfaces of aforesaid structures given by the definite level of densities.

A procedure of constructing polygonal surfaces includes the following steps:
  filtrating initial voxel models for diminishing a casual noise level;
  constructing a triangular surface on the basis of a <<marching cubes>> algorithm and <<exhaustion method>>, more known in English-written literature as an <<advancing front>> algorithm (1);
  smoothing the grid, i.e., constructing a polygonal surface close to the initial one but differing from it by lower values of angles between normal vectors of adjacent triangles (2);
  rarefying and quality-improving a grid, i.e., constructing a polygonal surface with a lower number of more large triangles close to equilateral ones (3).

<<Marching cubes>> algorithm allows one to construct a polygonal representation of isosurfaces given by a three-dimensional scalar field of densities (W. Lorensen, H. Cline Marching Cubes: A High Resolution 3D Surface Construction Algorithm Computer Graphics, 21(4): 163-169, July 1987).

The space is examined by displacement of a construction cube. Density values are determined at each step in vertices of this cube. When a density value in one of vertices of a cube edge is lower and in another one is higher than an isolevel, the surface aforesaid intersects this edge. After comparing density values for all vertices of a construction cube, it is determined what edges are intersected by an isosurface. Every variant of intersecting a construction cube by an isosurface defines a known set of triangles which is added in resultant grid.

For improving the quality of a triangular grid, the <<advancing front >> algorithm is used with the help of which constructing a new grid with monitored parameters is implemented on the basis of the grid obtained by the method of <<marching cubes>>. <<Advancing front >> algorithm is described in more detail in Lo S. H. Volume Discretization into Tetrahedra—II. 3D Triangulation by Advancing Front Approach//Computers and Structures, Pergamon, Vol. 39, No. 5, p.p. 501-511, 1991; Rassineux A. Generation and Optimization of Tetrahedral Meshes by Advancing Front Technique//International Journal for Numerical Methods in Engineering, Wiley, Vol. 41, p.p. 651-674, 1998; Gol'nik E. R., Vdovichenko A. A., Uspekhov A. A. Construction and Application of a Preprocessor of Generation, Quality Control, and Optimization of Triangulation Grids of Contact Systems//Information Technologies, 2004, No. 4, p. 2-10 [in Russian].

Algorithm of smoothing a triangular grid consists in the following. For each node of the grid with coordinates $P_0=(x_0, y_0, z_0)$, N of the nearest nodes $P_j=(x_j, y_j, z_j), j=1,2, \ldots, N$ are determined. The point Q=(x,y,z) which is an averaged position of this node $P_0$ and its neighbors is computed:

$$Q = \frac{\sum_{j=0}^{N} P_j}{N+1}.$$

Further, for node $P_0$, a vector r directed from this node to the point Q is computed. At each i-th step of the iterative process $P_0$ displaces to the direction of vector r:

$$P_0^{(i+1)} = P_0^{(i)} + \tau^{(i)} \cdot r^{(i)}.$$

The choice of a parameter $\tau$ is implemented so that a new node $P_0^{(i+1)}$ is maximally close to the point $Q^{(i)}$ with consideration of the following limitation: the displacement vector $\tau^{(i)} \cdot r^{(i)}$ has not to overstep the boundaries of a construction cube used in marching cubes algorithm:

$$\|\tau^{(i)} \cdot r^{(i)}\| < \lambda,$$

where $\|\ldots\|$ is the Euclidean norm of a vector, $\lambda$ is the length of a construction cube's edge.

This operation is repeated until the displacement of the node at i-th iteration gets less than a given value of stopping $\epsilon$ $$\|\tau^{(i)} \cdot r^{(i)}\| < \epsilon.$$

Algorithm for constructing a smoothed isosurface based on solution of the Poisson equation is also used (Kazhdan M., Bolitho M. and Hoppe H. Poisson Surface Reconstruction.— Eurographics Symposium on Geometry Processing, 2006). This algorithm may be applied to both an initial voxel field and a triangulation surface of poor quality.

A hierarchical splitting of the space into cubic regions, i.e., constructing an oct-tree, is implemented so that each terminal branch of oct-tree contains not more than N elements. A pronounced smoothing effect depends on the number N. Grid nodes are considered as oriented points (of vector) $V_i$ equal to unit normal vectors to a surface to be approximated. In the center of each j-th cubic element, so-called three-dimensional radial basis function (RBF) is given. As RBF, it is possible to use the Cauchy function:

$$f_j(x) = \frac{1}{1 + \|\overline{x}_j - x\|^2},$$

where $\overline{x}_j$ is the center of a cubic element, x is a random point of the space $\|\ldots\|$ is the Euclidean distance between points, as well as three-dimensional RBF of other kinds based on the Gaussian curve, etc.

In computational domain $\Omega$ a vector field $U(x)=(U_x(x), U_y(x), U_z(x))^T$ is introduced. This vector field is represented in the form of decomposition according to a system of RBF functions:

$$U_x(x)=\Sigma a_j \cdot f_j(x), U_y(x)=\Sigma b_j \cdot f_j(x), U_z(x)=\Sigma c_j \cdot f_j(x),$$

where $a_j, b_j, c_j$ are indefinite coefficients which are determined from the condition for the minimum of mean-square (standard) deviation of a vector-function U(x) from vectors $V_i$.

Based on obtained vector-function U(x), a scalar function $\phi(x)$ which meets the condition $\arg\min\|\text{grad}\phi(x)-U(x)\|_{L2}$ is found. This function $\phi(x)$ is found as solution of the Poisson equation $$\Delta\phi(x)=q(x)$$

in computational domain $\Omega$ with its own boundary conditions (Note 1) where q(x)=divU(x).

For solving the Poisson equation, the Galerkin projection method is applied which uses above-introduced RBF system as weight functions. Then, to obtained function $\phi(x)$ the marching cubes algorithm constructing a new polygonal approximation of the isosurface is applied.

Rarefying polygonal grids is performed according to the following algorithm.

For each triangle of a grid the parameter $\chi$ characterizing the quality of a triangle is computed according to one of the following formulas:

$$\chi = \frac{l_{min}}{\rho},$$

where $l_{min}$ is the minimal side of a triangle, $\rho$ is a radius of inscribed in a triangle circumference;

$$\chi = \frac{\rho_1}{\rho_2},$$

where $\rho_1$ is a radius of circumscribed circumference, $\rho_2$ is a radius of inscribed circumference;

$$\chi = \frac{l_{min}}{l_{max}},$$

where $l_{min}$ is the length of the smallest side of a triangle, $l_{max}$ the length of the greatest side of a triangle.

Further, for each triangle the parameter $\overline{\chi}$ is computed according to the formula:

$$\overline{\chi} = a_1 \cdot \chi + a_2 \cdot S_\Delta,$$

where $S_\Delta$ is the area of a triangle, $a_1, a_2$ are numerical coefficients which are chosen depending on the formula used for computing $\chi$ and on the required quality of a grid.

Afterwards, for each node of a grid the weight $\omega$ as arithmetical mean of values of parameters $\overline{\chi}_i$ of N triangles in which this node of a grid is a vertex:

$$\omega = \frac{\sum_{i=1}^{N} \overline{\chi}_i}{N}.$$

Then, the grid node with the lowest weight $\omega$ is removed, a hole formed is triangulated and changed weights of grid nodes are re-counted. The procedure is repeated until the quantity of triangles in a grid satisfies the given one.

FIG. 9 illustrates an automatic determination of coordinates of electrodes on CT or MRT data of the chest. Initial tomography data are filtrated with a given density threshold so that, as a result, those points are remained which correspond to the density level of electrodes. On the basis of a voxel model obtained by such a way, a triangulation grid with multi-connection structure is constructed by the marching cubes method. For each one-connection part the coordinates of geometrical center are calculated as arithmetical mean of coordinates of nodes. For each region the Euclidean distance from geometrical center to the nearest point of the torso surface is calculated. Regions with the Euclidean distance exceeding the given one are rejected. Geometric centers of remained regions are assumed to be Cartesian coordinates of electrodes. In accordance with an electrode-imposing scheme, electrode coordinates are sorted, and every number of an electrode is brought to conformity with its coordinates. The software provides an operator with opportunity to correct the position of electrodes in interactive mode.

Figure 10:
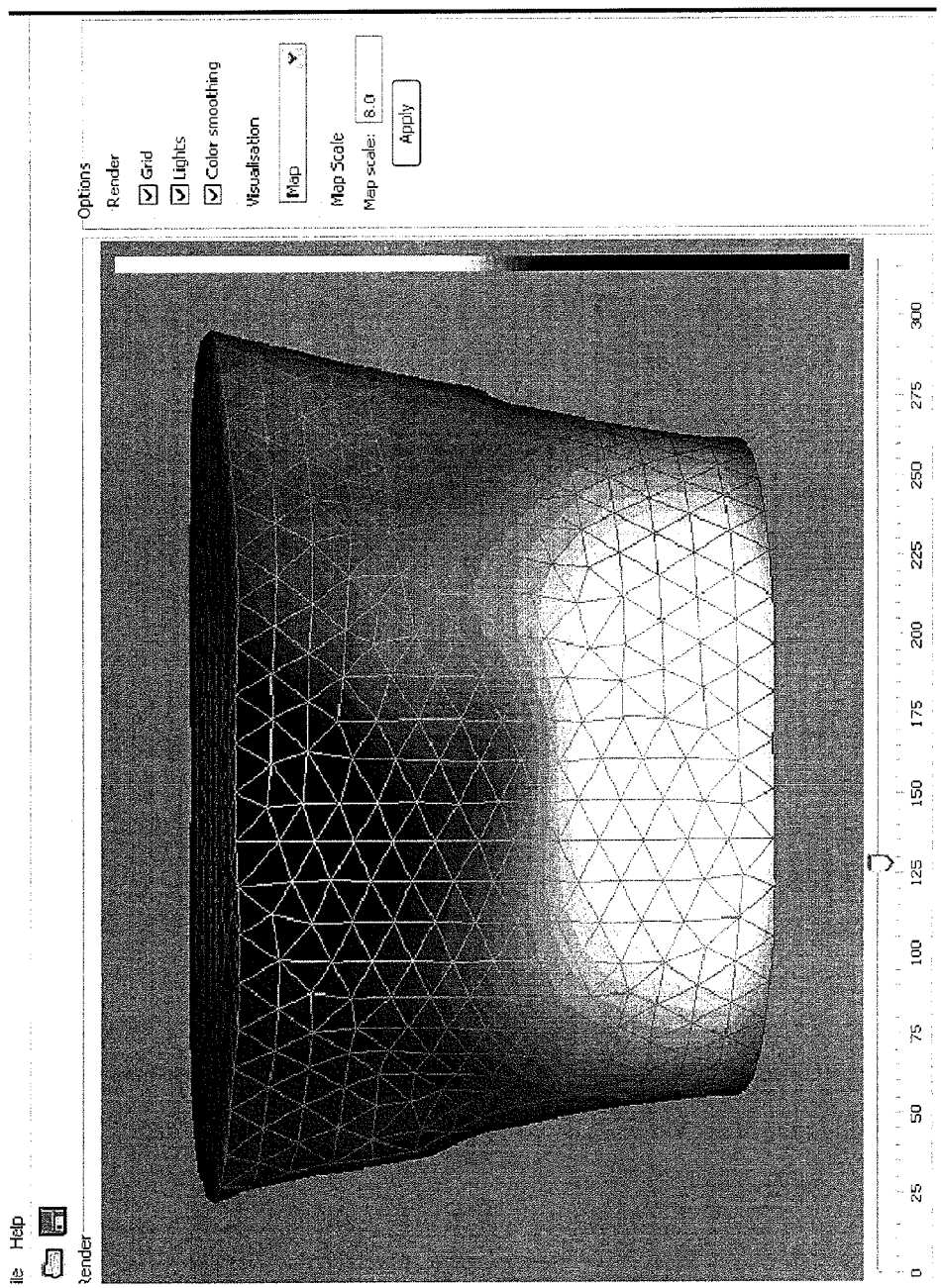
FIG. 10 presents isopotential maps on the torso surface.

FIG. 10 illustrates constructing isopotential maps on the torso surface.

This construction of isopotential maps is carried out by surface interpolation of values of ECG-signals at each discrete moment with using radial basis functions.

The electric field potential on the chest surface, S, is represented in the form of decomposition according to a system of radial basis functions (RBF):

$$U(x) = \Sigma a_j f_j(x), x \in S,$$

where $U(x)$ is the electric field potential, $f_j(x)$ are radial basis functions, $a_i$ are indefinite coefficients.

Functions of the following kind given at ECG-registration points are used as RBF:

$$f_j(x) = \exp\left(-\frac{\|x - x_j\|}{c^2}\right),$$

where x is a random point on the body surface, $x_j$ are ECG-registration points, $\|x-x_j\|$ is the smallest length of a line belonging to the surface S and connecting points x and $x_j$, c is an experimentally chosen coefficient which defines approximation properties of the function.

Coefficients $a_j$ are found from the condition for the minimum of functional J:

$$J = \frac{1}{2}\sum_{i=1}^{N}\left[\left(\sum_{j=1}^{N} a_j f_j(x_i) + a_0\right) - U(x_i)\right]^2$$

provided that $$\sum_{j=0}^{N} a_j = 0,$$

where $U(x_i)$ are values of the electric field potential at ECG-registration points $x_i$ on the chest surface, N is a number of ECG-registration points.

For finding coefficients $a_j$ the corresponding system of linear algebraic equations with a matrix of N×N size is solved.

The potential $U(x_i)$ is calculated in nodes of the triangulation torso surface $x_i$ according to the formula:

$$U(x_i) = \sum_{j=1}^{N} a_j f_j(x_i) + a_0.$$

To compute the potential at each point of the torso surface, a bilinear interpolation on values in vertices of a grid triangle, which this point belongs to, is applied.

The claimed method includes a method for noninvasive reconstructing the heart electric field potential at internal points of the chest based on measured values of the electric field potential on the chest surface by means of numerical solving the inverse problem of electrocardiography for an electrically homogenous model of the chest by the direct boundary element method on the basis of an iteration algorithm.

For realizing this method, the following model is used. Let $\Omega \in R^3$ be a part of the chest limited by a sufficiently smooth border $\partial \Omega$, which includes the torso surface contacting with external medium $\Gamma_B$ and cross-sections of the chest at the level of the diaphragm and clavicles $\Gamma_{T1}$ and $\Gamma_{T2}$ as well as the heart epicardial surface $\Gamma_E$. Chest tissues in domain $\Omega$ are assumed to have a constant positive limited coefficient of specific electroconductivity.

The heart electric field potential in domain $\Omega$ is assumed to satisfy the Laplace equation:

$$\Delta u(x) = 0, \qquad (4)$$

where $x=(x_1,x_2,x_3)^T \in \Omega \subset R^3$ is a point in three-dimensional (3-D) space, $$\Delta \equiv \frac{\partial^2}{\partial x_1^2} + \frac{\partial^2}{\partial x_2^2} + \frac{\partial^2}{\partial x_3^2}$$

is the Laplace operator in $R^3$.

The Dirichlet condition (electric field potential measured as a result of surface RCG mapping) at the part of border $\Gamma_B$ of domain $\Omega$ is assumed to be known:

$$u(x) = U_0(x), x \in \Gamma_B. \qquad (5)$$

The Dirichlet condition contains a noise component as a result of experimental measurements:

$$U_0(s) = u_0(s) + \xi(s), s \in \Gamma_B, \qquad (6)$$

where $u_0(s)$ is the exact value of potential on the chest surface, $\xi(s)$ is a measurement error estimated as $\xi(s) < \delta$.

At the same border part the condition is also known:

$$\frac{\partial u(x)}{\partial n} = P_0(x) = 0, x \in \Gamma_B, \qquad (7)$$

where $$\frac{\partial u(x)}{\partial n}$$

is a potential derivative $u(x)$ along an internal normal to the surface.

Solution of the inverse problem of electrocardiography consists in a harmonic continuation of the potential $u(x)$ from surface $\Gamma_B$ to surface $\Gamma_H = \Gamma_E \cup \Gamma_{T1} \cup \Gamma_{T2}$, i.e., in finding on surface $\Gamma_H$ a potential trace $u(x)$, which satisfies the Laplace condition (4) within domain $\Omega$ and boundary conditions (5)-(7) at the borders of regions.

For solving the inverse problem of electrocardiography the boundary element method is applied (Brebbia C., Telles J., Wrobel L. Boundary element techniques [Russian translation], Moscow, Mir (1987).

The external surface of the heart and surfaces bounding the chest are approximately substituted by a boundary-element grid, i.e., a polygonal surface consisting of $2 \cdot 10^3 - 5 \cdot 10^3$ plane triangles. Surface $\Gamma_B$ is split into M boundary elements $\omega_j: \Gamma_B = \bigcup_{j=1}^{M} \omega_j$. Surface $\Gamma_H$ is split into N boundary elements $\omega_j: \Gamma_B = \bigcup_{j=1}^{N} \omega_j$.

The potential u(s) and its normal derivative q(s) are represented in the form of decomposition according to the system of linearly independent finite basis functions $\omega_i(s)$:

$$u(s) = \sum_{i=1}^{N} u_i \cdot \varphi_i(s), \quad (8)$$

$$q(s) = \sum_{i=1}^{N} q_i \cdot \varphi_i(s),$$

where coefficients of decomposition $u_i$ and $q_i$ are values of the potential u(s) and its normal derivative q(s) in nodes of a boundary-element grid.

As a result, the following vectors are formed:

$q_h$ is an unknown vector of N size obtained as a result of boundary-element discretization of the function q(s), $s\in\Gamma_H$. This vector has the following structure: $q_h=(q(s_1), q(s_2), \ldots, q(s_N))^T$ where $s_j$ are points located in j-th nodes of a boundary-element grid on surface $\Gamma_H$, $q(s_j)$ are values of a normal potential derivative at these points.

$u_h$ is an unknown vector of N size obtained as a result of boundary-element discretization of the function u(s), $s\in\Gamma_H$. This vector has the following structure: $u_h=(u(s_1), u(s_2), \ldots, u(s_N))^T$, where $s_j$ are points located in j-th nodes of a boundary-element grid on surface $\Gamma_H$, $u(s_j)$ are sought-for values of the potential at these points.

$U_0$ is the known vector of M size obtained as a result of boundary-element discretization of the function $U_0(s)$, $s\in\Gamma_H$. This vector has the following structure: $U_0=(U(s_1), U(s_1), \ldots, U(s_N))^T$, where $s_j$ are points located in j-th nodes of a boundary-element grid on surface $\Gamma_B$ $U(s_j)$ are experimentally measured values of the potential at these points.

The direct boundary element method directly uses the Green's third (main) formula which connects values of the potential and its normal derivative at boundary surfaces $\Gamma$ with values of the potential within computational domain $\Omega$ in the form of an integral relationship:

$$2\pi u(x) = \int_\Gamma q(y) \cdot \frac{1}{|x-y|} ds - \int_\Gamma u(y) \cdot \frac{\partial}{\partial n_y} \frac{1}{|x-y|} ds, \quad (9)$$
$$x \in \Gamma, y \in \Gamma,$$

where $x=(x_1,x_2,x_3)^T$ is a fixed point and $y=(y_1,y_2,y_3)^T$ is a <<sliding>> one on surface $\Gamma$, $|x-y|\equiv \sqrt{(x_1-y_1)^2+(x_2-y_2)^2+(x_3-y_3)^2}$ is the Euclidean distance between points x and y, $$q(y) \equiv \frac{\partial}{\partial n_y} u(y)$$

is a normal potential derivative at point y, $$\frac{\partial}{\partial n_y}$$

is an operator of differentiation in the direction of a unit normal vector to surface $\Gamma$ at point $y\in\Gamma$, ds is a differential element of surface $\Gamma$.

Use of the Green's third formula for points laying on surfaces $\Gamma_B$ and $\Gamma_H$ yields a system of the Fredholm integral equations (of $1^{st}$ and $2^{nd}$ kinds) which may be written in the form of a system of two matrix-vector equations with two unknown vectors $u_h$ и $q_h$ after boundary-element discretization of functions u(s) and q(s) according to formulas (8)

$$\begin{cases} G_{BH} \cdot q_h - H_{BH} \cdot u_h = c_{bb} \\ G_{HH} \cdot q_h - H_{HH} \cdot u_h = c_{hb} \end{cases} \quad (10)$$

The following designations are used here.

$G_{BH}$ is a matrix of M×N size obtained as a result of discretization of integral:

$$\int_{\Gamma_H} \frac{1}{|x-y|} ds, x \in \Gamma_B, y \in \Gamma_H;$$

$G_{HH}$ is a matrix of N×N size obtained as a result of discretization of integral:

$$\int_{\Gamma_H} \frac{1}{|x-y|} ds, x \in \Gamma_H, y \in \Gamma_H;$$

$H_{BH}$ is a matrix of M×N size obtained as a result of discretization of integral:

$$\int_{\Gamma_H} \frac{\partial}{\partial n_y} \frac{1}{|x-y|} ds, x \in \Gamma_B, y \in \Gamma_H;$$

$H_{HB}$ is a matrix of N×M size obtained as a result of discretization of integral:

$$\int_{\Gamma_B} \frac{\partial}{\partial n_y} \frac{1}{|x-y|} ds, x \in \Gamma_H, y \in \Gamma_B;$$

$H_{HH}$ is a matrix of N×N size computed as $H_{HH}=\hat{H}_{HH}+2\pi E$, where $\hat{H}_{HH}$ is a matrix obtained as a result of discretization of integral $$\int_{\Gamma_H} \frac{\partial}{\partial n_y} \frac{1}{|x-y|} ds,$$

$x\in\Gamma_H$, $y\in\Gamma_H$, E—is an unit matrix;

$H_{BB}$ is a matrix of M×M size computed as $H_{BB}=\hat{H}_{BB}+2\pi E$, where $\hat{H}_{BB}$ is a matrix obtained as a result of discretization of integral $$\int_{\Gamma_B} \frac{\partial}{\partial n_y} \frac{1}{|x-y|} ds,$$

$x\in\Gamma_B$, $y\in\Gamma_B$, E—is an unit matrix;

$c_{bb}$ is a known vector of M size computed as $c_{bb}=H_{BB}\cdot U_0$;
$c_{hb}$ is a known vector of M size computed as $c_{hb}=H_{HB}\cdot U_0$.
For solving the system (10) the following iteration algorithm is used:

$$q_h^{(1)} = q_0 \quad (11)$$

$$H_{HH} \cdot u_h^{(2k)} = G_{HH} \cdot q_h^{2k-1} - c_{hb} \quad (12)$$

$$G_{BH} \cdot q_h^{2k+1} = H_{BH} \cdot u_h^{2k} + c_{bb} \quad (13)$$

where $q_0$ is a randomly given vector of initial approximating the N size, k=1,2, . . . ,n are iteration numbers.

At even step of the iteration process, $u_h^{2k}$ is found by solving SLAE (12) and is substituted in SLAE (13). At uneven step of the iteration process $q_h^{2k+1}$ is found by solving SLAE (13) and is substituted in SLAE (12).

For the determination of a number of iterations the principle of the residual (the Morozov principle) is used: a procedure is stopped at the iteration 2k starting from which the residual norm does not exceed an absolute error of a free term:

$$\|(G_{HH} \cdot q_h^{(2k-1)} - c_{hb}) - H_{hh} \cdot u_h^{2k}\| \leq \|\delta\| \quad (14)$$

where $\delta$ is an absolute error of determination of the electric field potential on the chest surface, $\|\ldots\|$ is any of vector norms.

Solution of SLAE (12) at each step of an iteration procedure is computed according to the formula $$u_h^{2k} = M_1 \cdot q_h^{2k-1} - c_1 \quad (15)$$

where $M_1 = (H_{HH})^{-1} \cdot G_{HH}$, $c_1 = (H_{HH})^{-1} \cdot c_{hb}$

Inversion of matrix $H_{HH}$ is implemented by standard algorithms of computational linear algebra (LU—decomposition, QR—decomposition, etc.). Since matrix $M_1$ and vector $c_1$ do not change in the course of implementing an iterative procedure, these matrix and vector are computed only once.

Solution of SLAE (13) at each step of an iteration procedure is computed on the basis of the Tikhonov regularization method: regularized solution $q_h^{(2k+1)}$ depending on a regularization parameter $\alpha$ is found as solution of SLAE:

$$[(G_{BH})^T \cdot G_{BH} + \alpha E] \cdot q_h^{(2k+1)} = (G_{BH})^T \cdot (H_{BH} \cdot u_h^{(2k)} + c_{bb}), \quad (16)$$

where $(G_{BH})^T$ is a matrix transponated regarding matrix $G_{BH}$, E is a unit matrix.

A regularization parameter $\alpha$ (positive real number) is computed according to the formula:

$$\alpha = \alpha_0 + \beta \cdot p^{31 \, (k/2)}, \quad (17)$$

where $\alpha_0$ is a small real parameter depending on an error of giving boundary conditions of the inverse problem of electrocardiography, p is a positive real parameter depending on the convergence velocity of an iterative procedure, $\beta$ is a positive real parameter depending on the accuracy of initial approximation in an iterative procedure, k is the iteration number.

Figure 11:
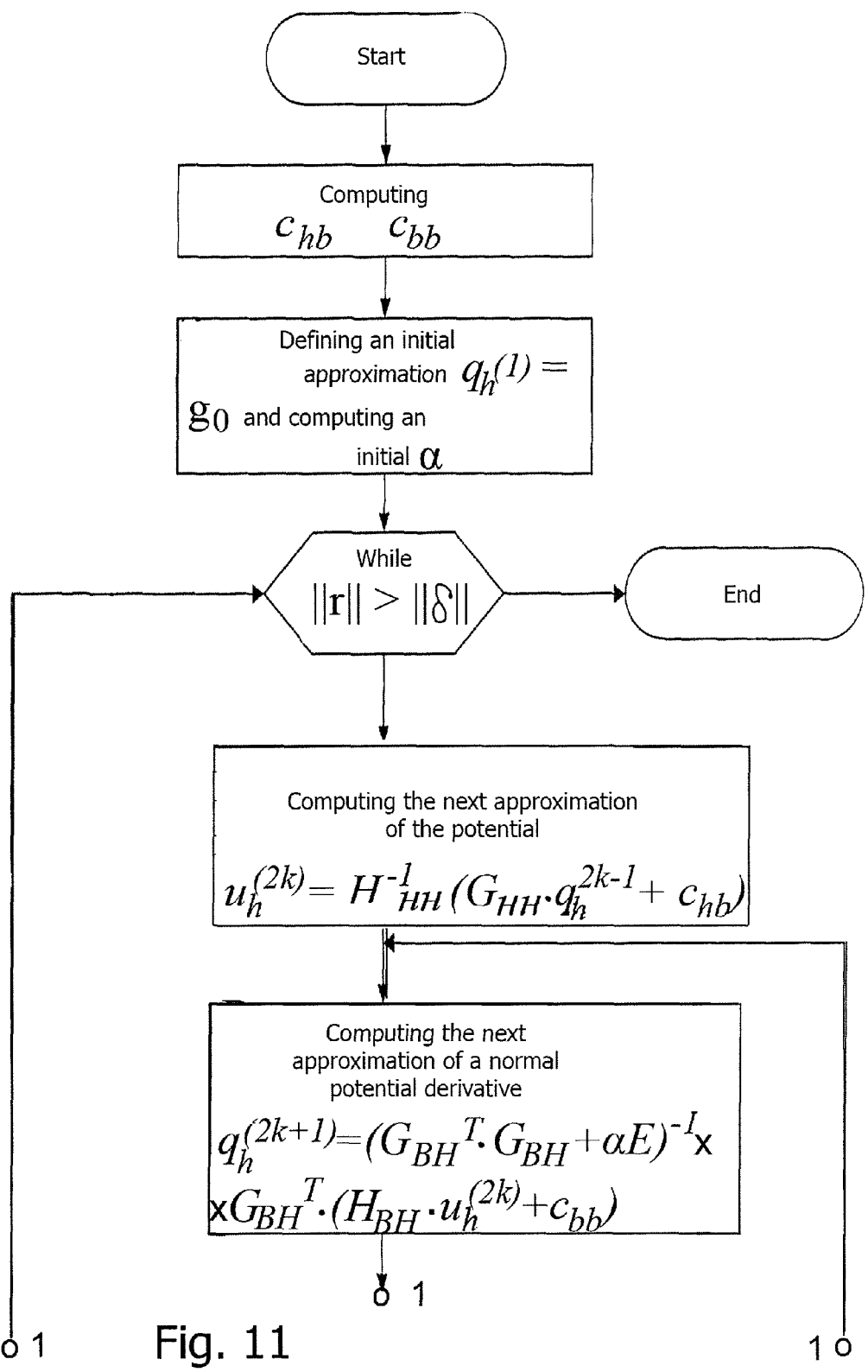
FIG. 11 shows a block-diagram of a computational algorithm of solution of the inverse problem of electrocardiography.
Figure 11:
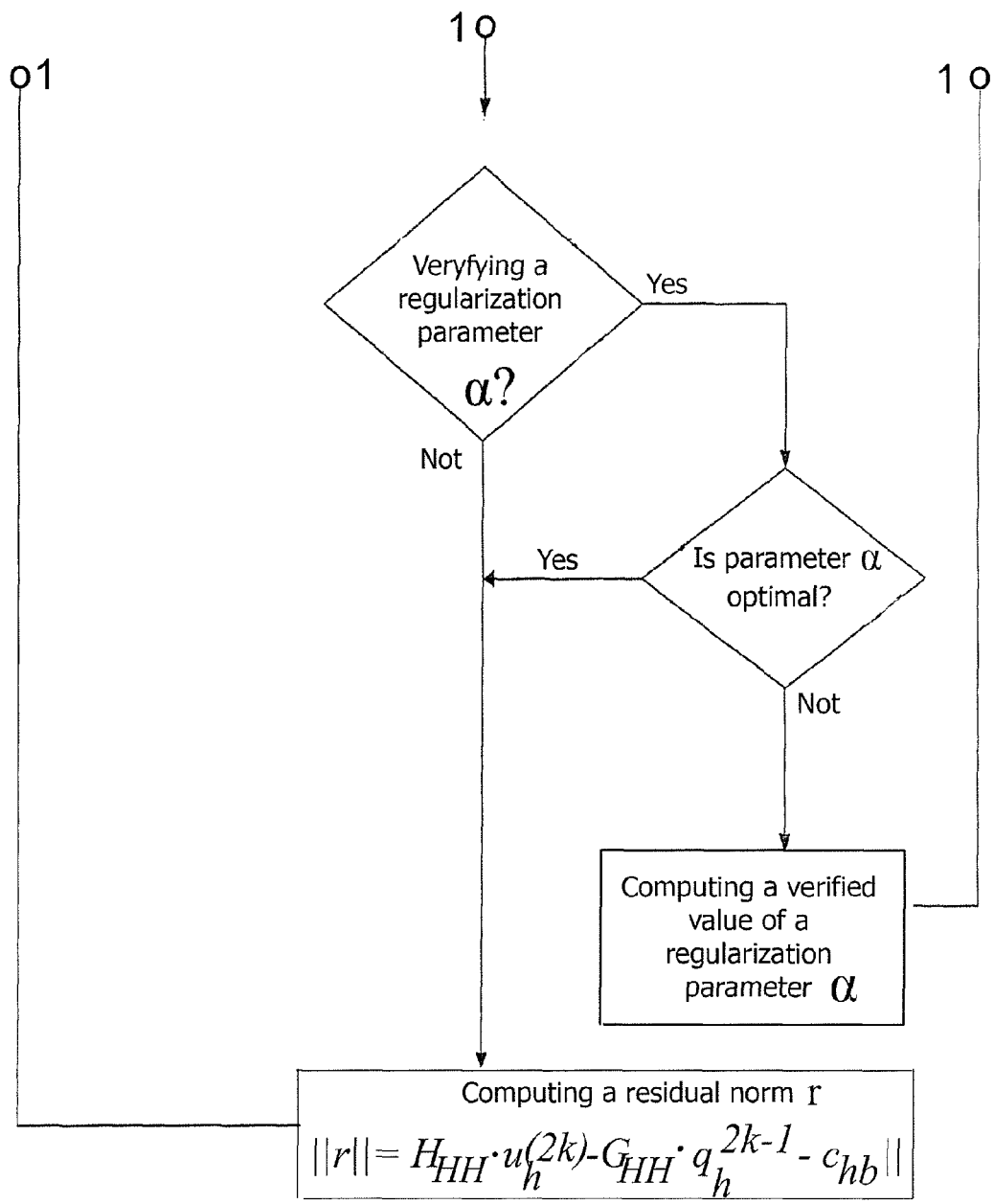

A block-diagram of algorithm is shown in FIG. 11.

FIG. 12 shows convergence diagrams of an iterative procedure with a constant regularization parameter $\alpha$ (13A) and with verifying this parameter at each iteration step $\alpha$ according to the formula cited above (FIG. 13B). The following parameters were used: $\alpha_0 = 10^{-7}$, $\beta = 10^4$, p=10.

In calculations, a model of the torso and heart of a real patient was used. The total number of triangle elements in a grid for the torso and heart was 2252. For modeling the standard electric field of the heart, a quadruple source to be placed in geometric center of the heart was used.

FIGS. 13 and 14 show results of reconstructing the electric field on the heart surface based on afore-cited algorithm and method disclosed in US Patent (Rudy Y., Ramanathan C., Ghanem R. N., Jia P. System and method for noninvasive electrocardiographic imaging (ECGI) using generalized minimum residual (GMRES)//U.S. Pat. No. 7,016,719 B2, 2006.) Parameters of algorithm disclosed in the present invention, parameters of a model for the torso and heart and parameters of the standard electric field were the same as in previous example. For calculations in accordance with a method proposed by Rudy Y. et al. a GMRes—algorithm version realized in the MatLab (R 14) medium was used. Parameters of GMRes—algorithm (a number of iterations before the next re-start and the total number of iterations) were determined by an experimental way based on the accuracy of reconstruction. The number of iterations before the next re-start was 234; the total number of iterations was 2340.

FIG. 13A shows diagrams of the standard potential and potential reconstructed by algorithm disclosed. FIG. 13B shows diagrams of the standard potential and potential reconstructed by algorithm proposed by Rudy Y. et al. The abscissas axis represents an index number of a boundary-element node; the ordinates axis represents a value of the potential in the corresponding node. Nodes were put in proper order in accordance with exact values of the potential in this node. The exact value of potential is marked by red and the reconstructed value of potential is marked by blue.

FIG. 14 presents imposed on a realistic models of the heart isopotential maps of the exact electric potential (14A) calculated by algorithm (14B) disclosed in the present invention, reconstructed by algorithm proposed by Rudy Y. et al. (14C) (upper row is a front view; lower one—a view from behind-below).

The method comprises an iterative method for solving a system of matrix-vector equations (10) in which at each step SLAE (13) is solved with using a pseudo-inversion of a matrix on the basis of SVD-decomposition with filtration of singular numbers to be small on module.

Regularizing solution of SLAE (13) $q_h^{(2k+1)}$ depending on a parameters $\epsilon$ is found according to the formula:

$$q_h^{2k+1} = (G_{BH})_\epsilon^+ \cdot H_{BH} \cdot u_h^{2k} + (G_{BH})_\epsilon^+ \cdot c_{bb},$$

where $(G_{BH})_\epsilon^+$ is the regularized pseudo-inverse matrix depending on a parameter $\epsilon$.

Matrix $(G_{BH})$: is computed as follows. Matrix $G_{BH}$ of M×N size is represented in the form of SVD-decomposition: $G_{BH} = U\Sigma V^T$ where U is an orthogonal matrix of M×M size, V is an orthogonal matrix of N×N size, $\Sigma$ is a diagonal matrix of M×N size on whose main diagonal singular numbers of matrix $G_{BH}$ are arranged in diminishing order; the remaining elements are equal to zero. Computing SVD-decomposition of matrix $G_{BH}$ is performed by one of standard algorithms of computational linear algebra (QL—algorithm, QR—algorithm, etc.).

All non-zero singular numbers $\sigma_j$ of matrix $\Sigma$ for which the condition $\sigma_j < \epsilon$ is true are substituted by zeroes. Further, a regularized pseudo-inverse matrix $\Sigma^+$ is constructed: non-zero diagonal elements $\sigma_j$ of matrix $\Sigma$ are conferred by meanings of $$\frac{1}{\sigma_j}.$$

Afterwards, regularized pseudo-inverse matrix $(G_{BH})_\epsilon^+$ depending on a parameter $\epsilon$ is constructed according to the formula:

$$(G_{BH})^+ = V\Sigma^+ U^T.$$

Parameters $\epsilon$ which plays the role of a regularization parameter is determined by the formula:

$\epsilon = \epsilon_0 + \beta \cdot P^{-(k/2)}$ where $\epsilon_0$ is a small real parameter depending on an error of defining boundary conditions of the inverse problem of electrocardiography, p is a positive real parameter depending on the convergence velocity of an iterative procedure, β is a positive real parameter depending on the accuracy of initial approximation in an iterative procedure, k is the iteration number.

The method comprises an iterative method for solving a system of matrix-vector equations under consideration (10), in which at each iteration step SLAE (12) and (13) are solved also by an iterative method based on generalized minimal residual (GMRes) algorithm for non-square matrices.

The description of GMRes-algorithm used in the present invention, see Saad Y. Iterative Methods for Sparse Linear Systems (2nd ed.), SIAM, Philadelphia (2003).

When solving SLAE (12), iterations of GMRes-algorithm are stopped as soon as the following condition is fulfilled:

$$\|u^{(2k)} - u^{(2k-2)}\| < \epsilon_1$$

or $$\|(G_{HH} \cdot q_h^{(2k-1)} - c_{hb}) - H_{HH} \cdot u_h^{(2k)}\| < \epsilon_2$$

where $\|\ldots\|$ is the Euclidean norm of a vector, k is the iteration number, $\epsilon_1$, $\epsilon_2$ are small parameters depending on the machine accuracy.

When solving SLAE (13), a number of iterations of GMRes-algorithm is determined by the formula:

$$n = n_0 + \lambda \cdot k,$$

where n is a number of iterations of GMRes—algorithm, k is the iteration number in the procedure (11)-(13), $n_0$ and $\lambda$ are positive whole numbers depending on the accuracy of initial approximation and the convergence velocity of the procedure (11)-(13).

The method includes an iterative method for solving a system of matrix-vector equations (10) with matrices of high size, in which at each step of the iterative procedure SLAE (12), (13) are solved based on the fast multipole method.

For solving SLAE (12),(13) at each step of an iterative procedure, an iterative method for non-square matrices is applied that includes only the operations of matrix-vector addition (subtraction) and multiplication of matrix by vector, for instance, a generalized minimal residual (GMRes) algorithm.

Figure 15:
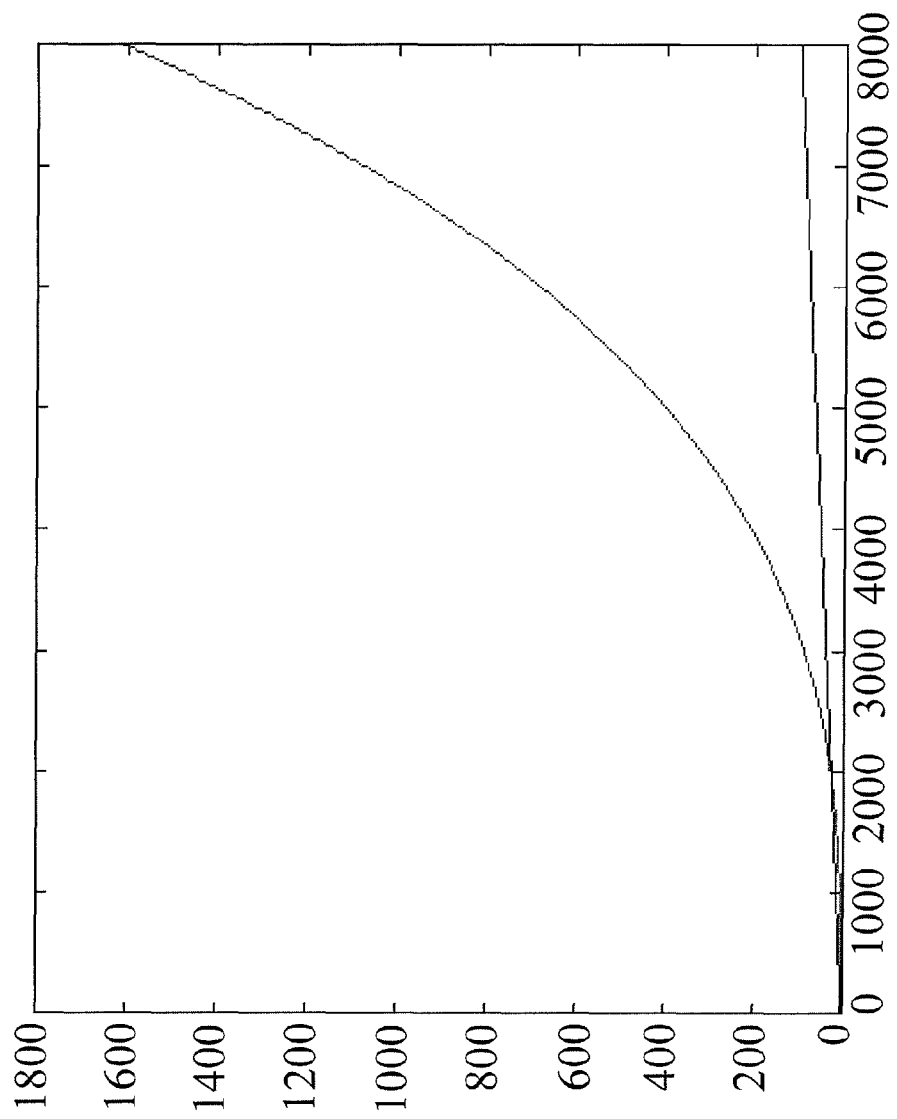
FIG. 15 illustrates the potentiality of the "fast multipole method". In the left column from above, a scheme of operations for realizing classical BEM is shown, from below—a scheme of operations for realizing FMM BEM. In the right column, a scheme of a hierarchical space splitting and details of realizing the FMM BEM method are depicted.

For realizing the operation of multiplication of matrix by vector, the fast multipole method presented in FIG. 15 is used. It is described in more details in Yoshida K. Applications of fast multipole method to boundary integral equation method. Ph.D. Dissertation, Department of Global Environment Engineering, Kyoto University (2001). The main idea of this method is disclosed in FIG. 15, left panel.

Realizing the fast multipole method includes the following steps (FIG. 15, right panel):
1. A hierarchical splitting of a computational domain $\Omega$ into sub-domains, i.e., constructing an oct-tree, is implemented.
2. Kernels of integrals $$\int_{\Gamma_H} \frac{1}{|x-y|} ds, x \in \Gamma_B, y \in \Gamma_H, \int_{\Gamma_H} \frac{1}{|x-y|} ds, x \in \Gamma_H, y \in \Gamma_H,$$

$$\int_{\Gamma_H} \frac{\partial}{\partial n_y} \frac{1}{|x-y|} ds, x \in \Gamma_B, y \in \Gamma_H,$$

$$\int_{\Gamma_H} \frac{\partial}{\partial n_y} \frac{1}{|x-y|} ds, x \in \Gamma_H, y \in \Gamma_H,$$

-continued $$\int_{\Gamma_B} \frac{\partial}{\partial n_y} \frac{1}{|x-y|} ds, x \in \Gamma_B, y \in \Gamma_B,$$

$$\int_{\Gamma_B} \frac{\partial}{\partial n_y} \frac{1}{|x-y|} ds, x \in \Gamma_H, y \in \Gamma_B$$

whose discretization results in the formation of matrices $G_{BH}$, $G_{HH}$, $H_{BH}$, $H_{HH}$, $H_{BB}$, $H_{HB}$ are divided to x and y variables based on decomposition in series, like a system of spherical functions, (multipole decomposition) regarding given nodes x, and y, in sub-domains of a hierarchical splitting of a computational domain.

3. Multipole moments in leaves of oct-tree are computed based on above-mentioned multipole decomposition.
4. Multipole moments for parents' levels of oct-tree are computed on the basis of earlier computed multipole moments (M2M).
5. Values of functions at remote points are computed based on earlier computed multipole moments (M2L, L2L).

A comparative diagram of the temporal complexity of the classical boundary element method and the fast multipole method is shown in FIG. 15 (continued).

Examples of visualizing results of noninvasive electrophysiological study of the heart are presented in FIG. 16.

Figure 16D:
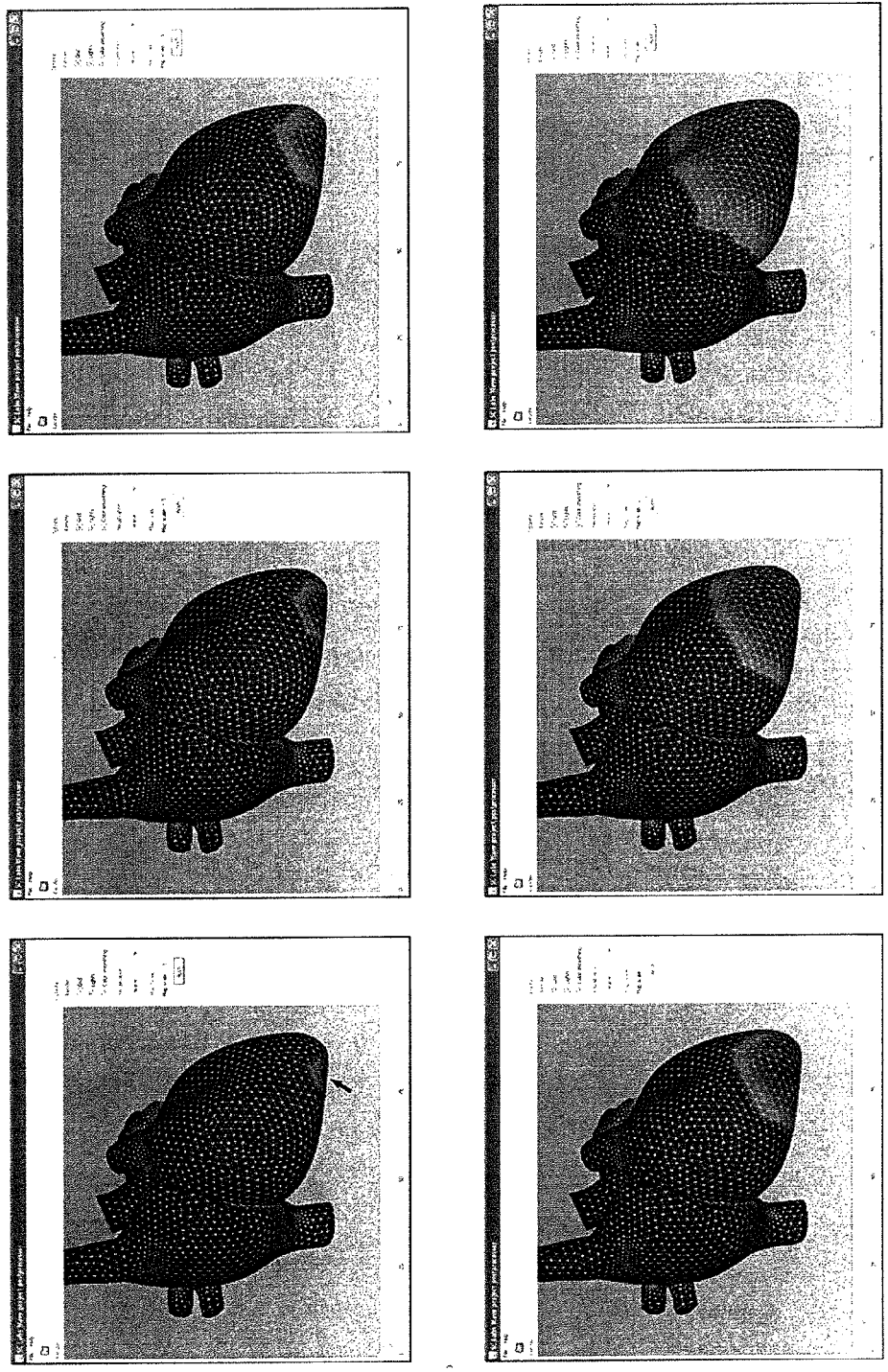
FIG. 16 shows examples of visualizing results of noninvasive electrophysiological study of the heart.

The following kinds of visual representation are used:
1. Constructing electrograms at interactively chosen points of the heart epicardial surface, endocardial surfaces of interventricular and interatrial septa, as well as at internal points of the chest on tomography cross-sections (FIG. 16A).
2. Constructing isopotential maps on tomography cross-sections of the chest (FIG. 16B).
3. Constructing isopotential and isochronous maps on the heart epicardial surface, endocardial surfaces of interventricular and interatrial septa (FIG. 16C).
4. Visualizing dynamics of the myocardium excitation on the heart epicardial surface, endocardial surfaces of interventricular and interatrial septa in animation mode (propagation maps) (FIG. 16D).

Unipolar electrograms are constructed by interpolation of computed values of the heart electric field potential for all moments of the cardiocycle at a given point. Bipolar electrograms are constructed as the difference of electrograms in a node chosen and at the point located in the vicinity to this node at a distance $\Delta l$ in the direction of l. Parameters $\Delta l$ and l are interactively given.

Isopotential maps are constructed on the basis of bilinear interpolation of computed values of the heart electric field potential in grid nodes at a given discrete moment of the cardiocycle by a gradient painting method or method for constructing isopotential lines.

For constructing isochronous maps two modes—manual and automatic—are provided. In manual mode in interactively chosen node of a grid an unipolar electrogram U(t), a bipolar electrogram $U_b = U_1(t) - U_2(t)$, as well as a differential electrogram $$U^l(t) = \frac{dU(t)}{dt},$$

i.e., a diagram of first derivative of an unipolar electrogram over time, are reconstructed. An operator, in interactive mode, marks in this diagram a time point τ which corresponds to the start of the myocardium activation at a given point. In automatic mode, the choice of a corresponding mark of time point r proceeds without operator's interference. The time point τ is determined as the maximum of a negative differential unipolar electrogram:

$$\tau = \max\left(-\frac{dU(t)}{dt}\right).$$

Isochronous maps are visualized on the basis of bilinear interpolation of τ values in grid nodes by means of gradient painting or constructing isochronous lines. The same data are represented in animation mode in the form of so-called propagation maps.

Figure 17:
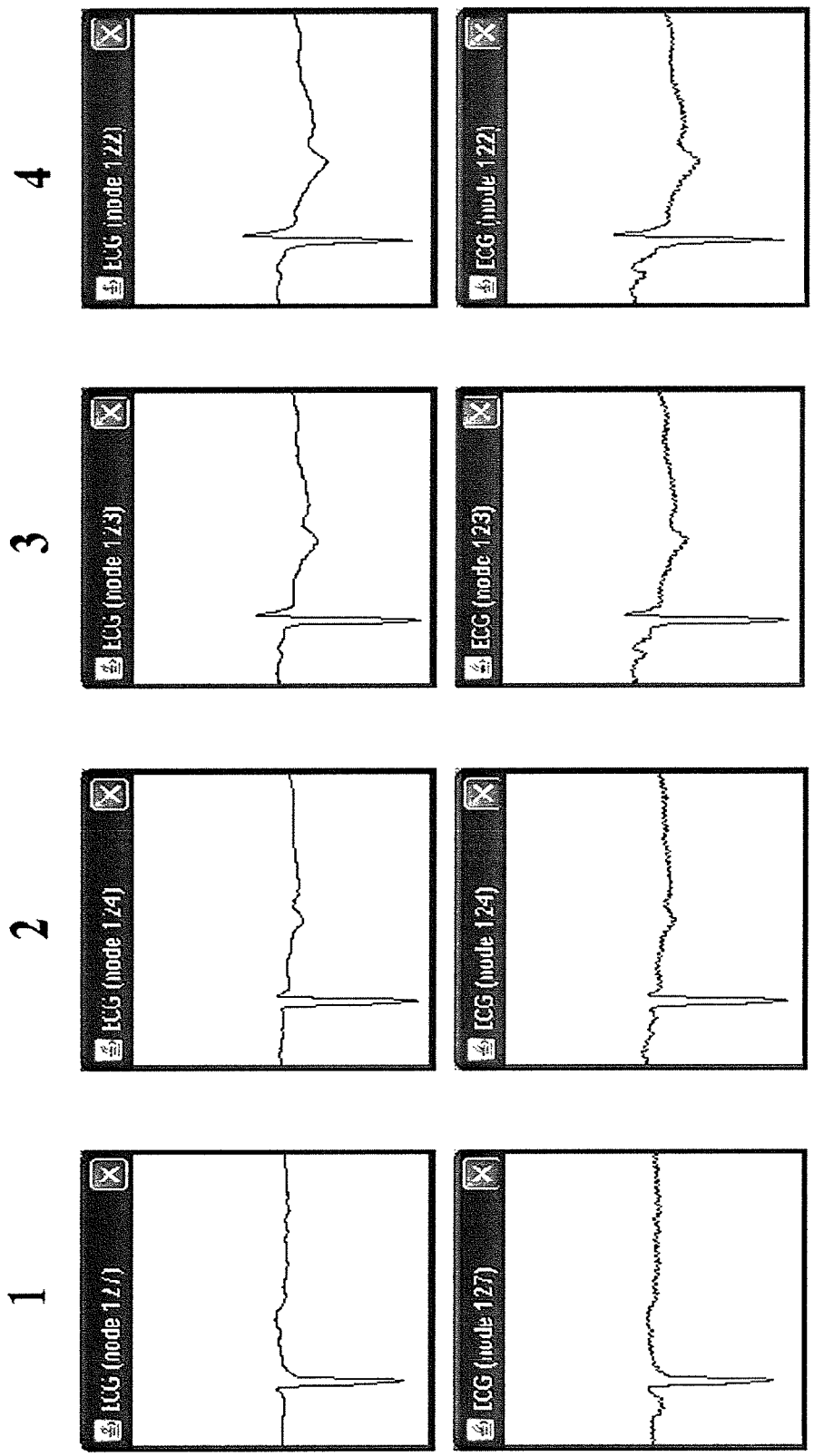
FIG. 17 compares intraesophageal electrograms reconstructed by the method under consideration with experimentally registered electrograms.
Figure 17:
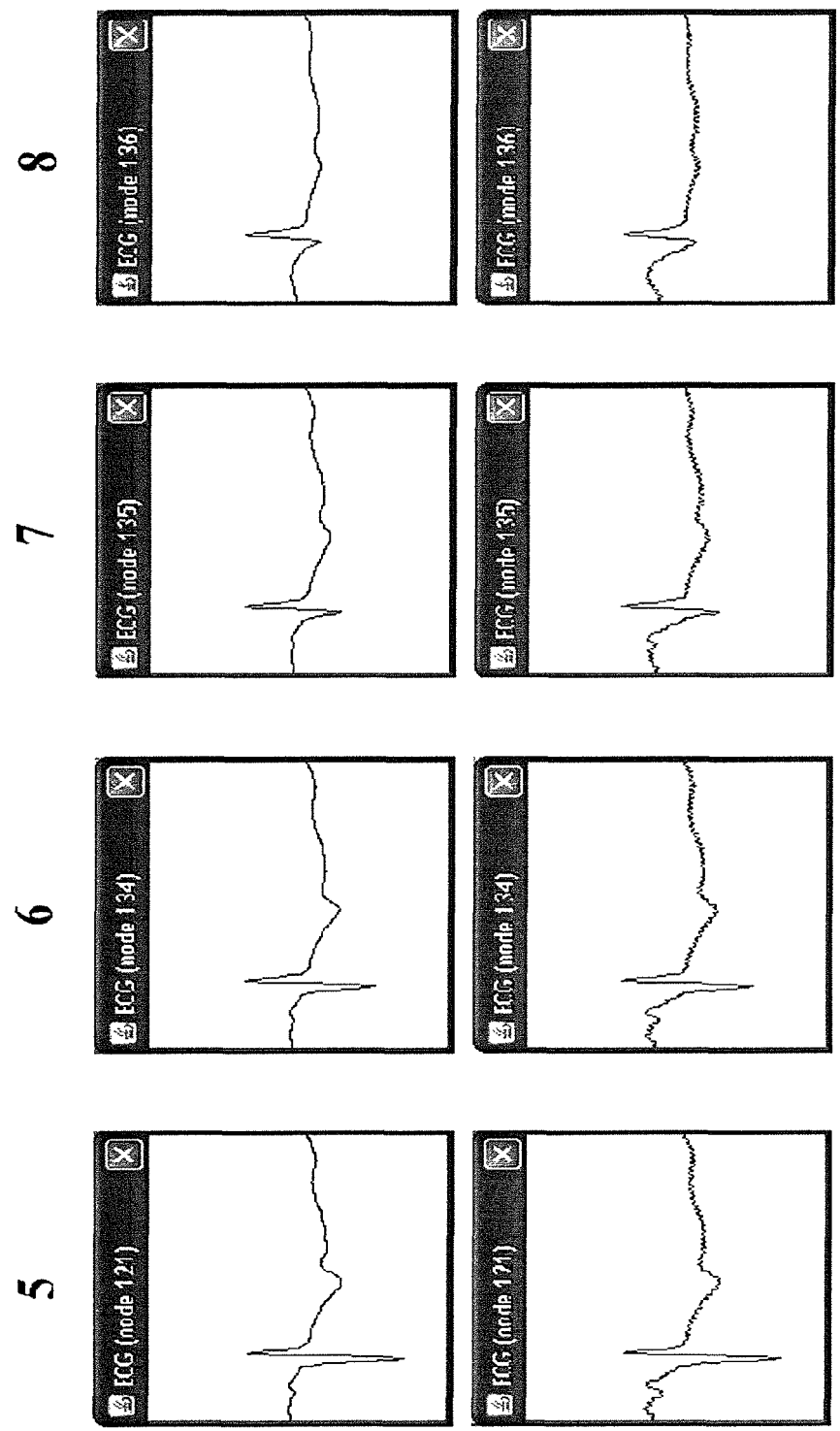

FIG. 17 depicts electrograms experimentally registered in the course of transesophageal electrophysiological study in six intraesophageal leads (upper row) and electrograms reconstructed at the same points by above-described way (lower row). When reconstructing, coordinates of intraesophageal electrodes were determined on data of computer tomography of the chest. Mean square relative error of reconstruction was 4%-6% what proved a sufficiently high accuracy of the method.

Figure 18:
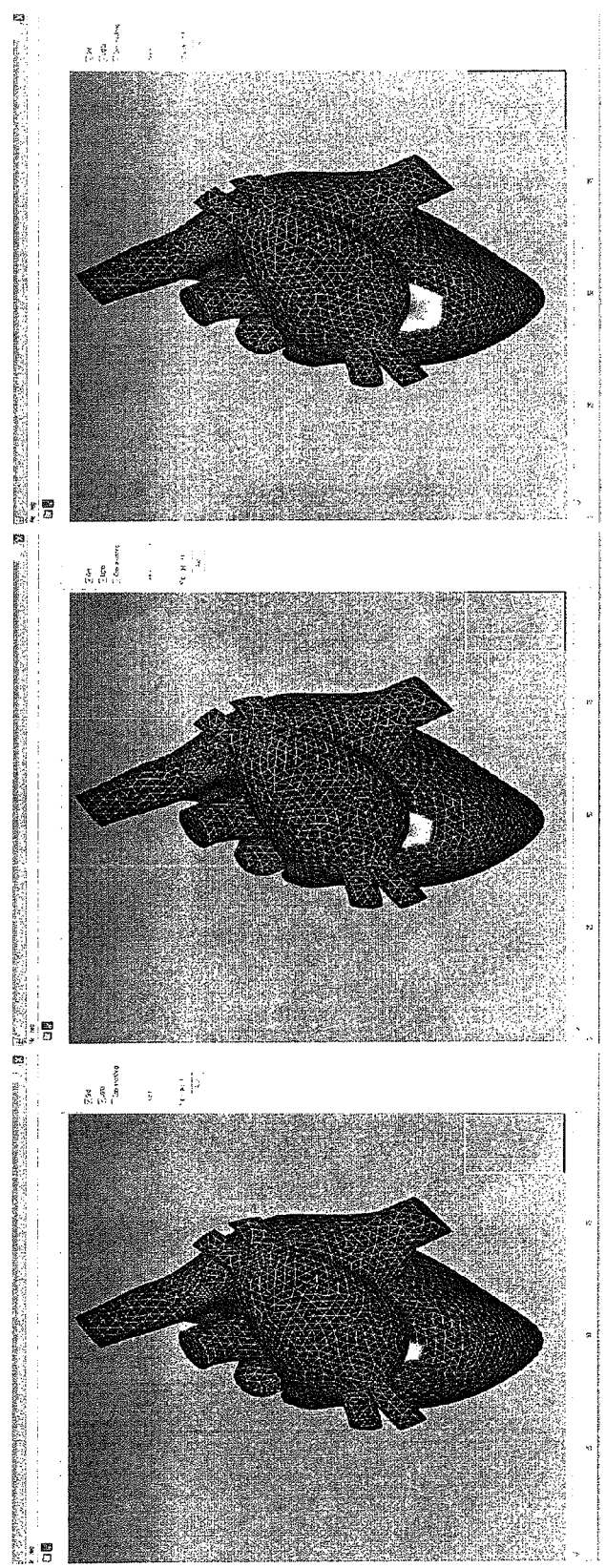
FIG. 18 presents epicardial, isochronous maps reconstructed by the method under consideration at manifested WPW syndrome of the left lateral localization in comparison with isochronous maps obtained on the basis of invasive endocardial mapping.

FIG. 18 shows reconstructed by the described method epicardial isochronous maps at manifested WPW syndrome of the left lateral localization (FIG. 18A) in comparison with isochronous maps obtained on the basis of invasive endocardial mapping with using CARTO system. The array indicates a localization of an ablation electrode with the help of which a successful radio-frequency ablation of an additional pathway was implemented.

Figures above demonstrate the high accuracy of coinciding isochronous maps obtained by an invasive way and based on the described method as well as the high accuracy of determining a localization of the additional pathway.

Figure 19:
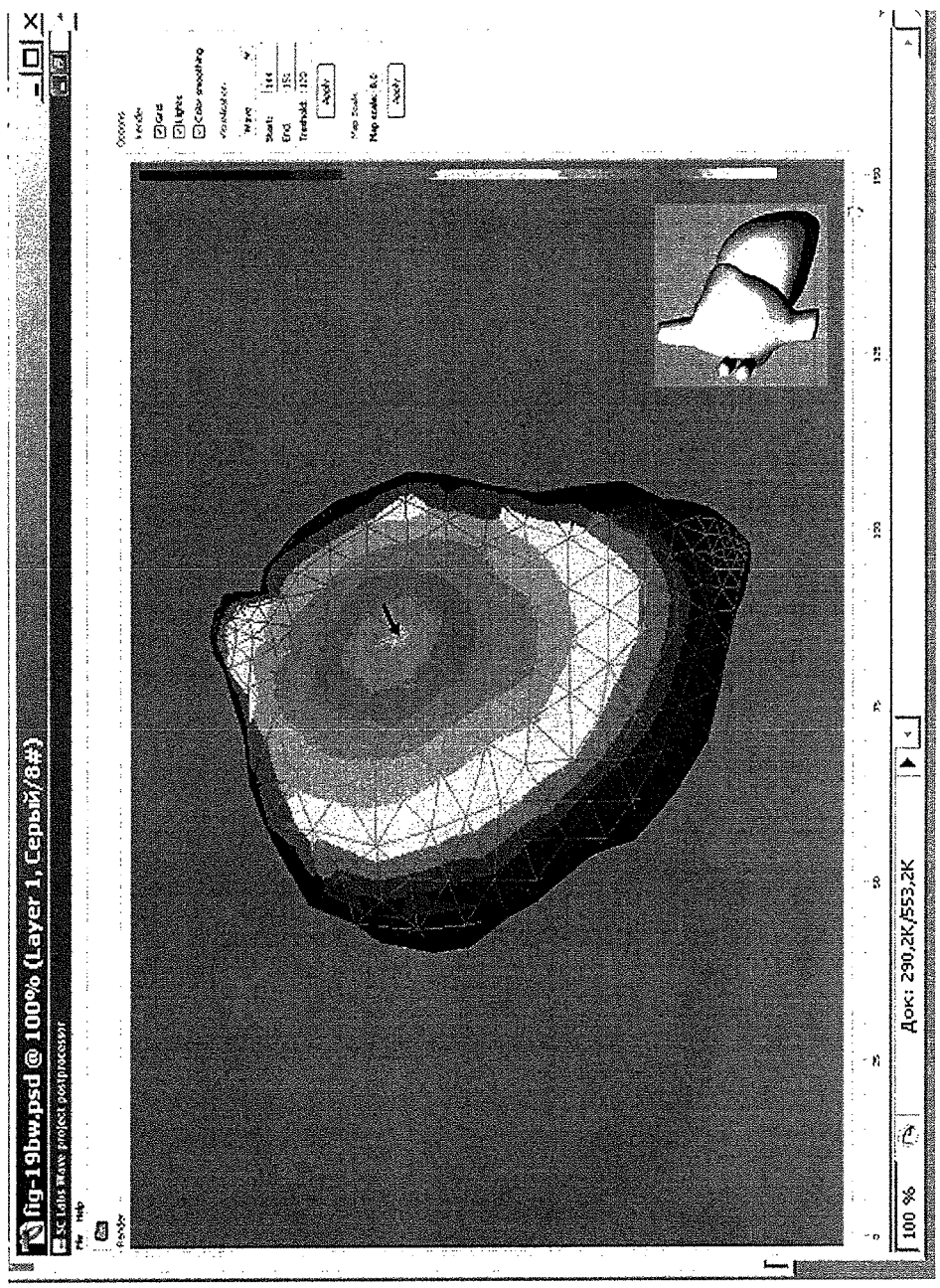
FIG. 19 shows results of noninvasive activation mapping of interventricular septum in a patient with ectopical ventricular extrasystole.

FIG. 19 depicts a reconstructed by the disclosed method isochronous map on the right surface of interventricular septum in a patient with ectopic ventricular extrasystole, a source of which was localized in interventricular septum. The array indicates a localization of an ablation electrode with the help of which a successful radio-frequency ablation of an additional pathway was implemented. FIG. 19 demonstrates the high accuracy of establishing a localization of an arrhythmia source.

What is claimed is:
1. A method of noninvasive electrophysiological study of the heart, comprising the following steps:
attaching one-off registration electrodes on a chest surface,
ECG-registering in several unipolar leads from the chest surface;
processing ECG-signals in real-time mode,
retrospective processing the ECG signals,
generating a computer (CT) or magneto-resonance (MRT) tomography
of the chest of a patient with the attached electrodes,
constructing and editing computer voxel models of organs of the chest and the heart,
constructing polygonal models of a torso and the heart with the help of a computer program;
determining coordinates of the registration electrodes on the chest surface;
interpolating values of the ECG-signals in nodes of a polygonal grid and obtaining isopotential maps on a polygonal model of the torso;
reconstructing an electric field potential at given points of the chest, epicardial surface of the heart, interventricular, and interatrial septa surfaces;
producing a visualization of results of reconstructing the heart electric field including epicardial electrograms, isochronous and isopotential maps, and propagation maps on the models of the heart and its structures; and
clinically evaluating the results.

2. The method according to claim 1, further comprising using metal chlorine-silver electrodes for CT and sticky graphite electrodes for MRT.

3. The method according to claim 1, wherein the one-off electrodes are attached in the form of horizontal 5-8 strips positioned at similar distances along a vertical, a first strip being positioned at the level of a sterno-clavicular articulation and a last one being positioned at the level of lower edge of the rib surface, each strip including from 16 to 30 electrodes positioned at similar distances in a circumference of the chest.

4. The method according to claim 1, further comprising using a shear-warp factorization of the viewing transformation algorithm for constructing the voxel model.

5. The method according to claim 1, wherein said step of constructing polygonal models comprises the following substeps:
filtrating the initial voxel models for diminishing a level of casual noises;
constructing a triangulation surface by a marching cubes method or an advancing front method;
rarefying and improving a quality of a grid using a Poisson surface reconstruction method.

6. The method according to claim 1, further comprising carrying out said step of determining coordinates of registration electrodes in automatic mode on the CT or MRT data of the chest.

7. The method according to claim 1, further comprising implementing said step of interpolating values of the ECG signals of the polygonal grid using radial basis functions.

8. The method according to claim 1, including performing said step of reconstructing the heart electric field potential by a numerical solution of a Cauchy problem for a Laplace equation using a boundary element method including an iteration solution of a final system of matrix-vector equations, for solving a second equation of said system regularizing methods being used, a total number of algorithm iterations being determined according to principle of a residual also known as a Morozov principle.

9. The method according to claim 8, further comprising applying, for solving the second equation of said system of matrix-vector equations, a Tikhonov regularization method, a regularization parameter being determined according to the formula $$\alpha = \alpha_0 + \beta \cdot p^{-(k/2)}, \quad (17)$$

where α is a regularization parameter; $\alpha_0$ is a small real parameter depending on an error of defining boundary conditions of an inverse problem of electrocardiography; p is a positive real parameter depending on a convergence velocity of an iterative procedure; β is a positive real parameter depending on an accuracy of initial approximation in an iterative procedure;
and k is the iteration number.

10. The method according to claim 8, further comprising using, for solving the second equation of said system of matrix-vector equations, a regularizing algorithm based on an SVD-decomposition of a matrix of the equation with substitution by zeroes of singular numbers which are less than a given positive number $\epsilon$, the parameter $\epsilon$ being determined according to the formula:

$$\epsilon=\epsilon_0+\beta\cdot p^{-(k/2)},$$

where $\epsilon_0$ is a small real parameter depending on an error of defining boundary conditions of an inverse problem of electrocardiography; p is a positive real parameter depending on a convergence velocity of an iterative procedure; $\beta$ is a positive real parameter depending on an accuracy of an initial approximation in an iterative procedure; and k is the iteration number.

11. The method according to claim 8, further comprising using, for solving the second equation of a system of matrix-vector equations, a regularizing algorithm based on an iterative generalized minimal residual method with restricting a number of iterations, a required number of iterations being determined according to the formula:

$$n=n_0+\lambda\cdot k,$$

where n is a number of algorithm iterations; k is the iteration number in a general iterative procedure; and $n_0$ and $\lambda$ are positive whole numbers depending on an accuracy of initial approximation and a convergence velocity of a procedure (11)-(13).

12. The method according to claim 8, further comprising solving equations of a system of matrix-vector equations based on a fast multipole method.

* * * * *